(12) United States Patent
Qu et al.

(10) Patent No.: US 9,840,741 B2
(45) Date of Patent: Dec. 12, 2017

(54) CIRCULATING MICRORNA AS A MARKER FOR HEPATOCELLULAR CARCINOMA

(75) Inventors: Kevin Qu, Lake Forest, CA (US); Ke Zhang, San Clemente, CA (US); Maher Albitar, Coto De Caza, CA (US)

(73) Assignee: QUEST DIAGNOSTICS INVESTMENTS INCORPORATED, Wilmington, DE (US)

( * ) Notice: Subject to any disclaimer, the term of this patent is extended or adjusted under 35 U.S.C. 154(b) by 273 days.

(21) Appl. No.: 13/047,659

(22) Filed: Mar. 14, 2011

(65) Prior Publication Data

US 2011/0281268 A1 Nov. 17, 2011

Related U.S. Application Data

(60) Provisional application No. 61/313,677, filed on Mar. 12, 2010.

(51) Int. Cl.
*C12Q 1/68* (2006.01)
*G01N 33/574* (2006.01)
*C07H 21/02* (2006.01)

(52) U.S. Cl.
CPC ..... *C12Q 1/6886* (2013.01); *G01N 33/57438* (2013.01); *C12Q 2600/178* (2013.01); *G01N 2333/471* (2013.01)

(58) Field of Classification Search
CPC ............ C12Q 1/6886; C12Q 2600/178; G01N 2333/471; G01N 33/57438
See application file for complete search history.

(56) References Cited

U.S. PATENT DOCUMENTS

2008/0254473 A1* 10/2008 Chen et al. .................. 435/6

OTHER PUBLICATIONS

Yamamoto, Y et al., Biomarkers, vol. 14, pp. 529-538 (2009).*
Shigoka, M. et al. (Pathol. Int., vol. 60, pp. 351-357 (2010).*
Xu, J. et al., Mol. Carcinogen., vol. 50, pp. 136-142 (2011).*
Gui, J. et al., Clin. Science, vol. 120, pp. 183-193 (2011).*
Zhou, J. et al., J. Clin. Oncol., vol. 29, pp. 4781-4788 (2011).*
McDonald, J.S. et al., Clin. Chem., vol. 57, pp. 833-840 (2011).*
Elfimova, N. et al., Frontiers in Physiol., vol. 3, Article 476, pp. 1-6 (2012).*
Wang, X. et al., Plos One, vol. 9, e86792, pp. 1-8 (2014).*
TaqMan MicroRNA Assays Protocol, Applied Biosystems (Jun. 2005).*
Mitchell, P.S. et al., PNAS USA, vol. 105, pp. 10513-10518 (2008).*
Chen, X. et al., Cell res., vol. 18, pp. 997-1006 (2008).*
Chim, S.S.C. et al., Clin. Chem., vol. 54, pp. 482-490 (2008).*
Gilad, S. et al., PlosOne, vol. 3, e3148, pp. 1-7 (2008).*
Hunter, M.P. et al., PLoS One, vol. 3, e3694, pp. 1-11 (2008).*
Office Action issued on Dec. 18, 2012 by the Examiner in U.S. Appl. No. 13/046,187.
Wang et al., "Circulating microRNA's potential biomarkers for drug-induced liver injury," PNAS, vol. 106, No. 11, Mar. 17, 2009.

(Continued)

*Primary Examiner* — Teresa Strzelecka
(74) *Attorney, Agent, or Firm* — Foley & Lardner LLP

(57) ABSTRACT

Provided herein are methods for the diagnosis, or management of liver diseases, e.g. hepatocellular carcinoma, using profiles of the miRNAs determined from cellular or acellular body fluids.

5 Claims, 2 Drawing Sheets

(56) References Cited

OTHER PUBLICATIONS

Braconi et al, MiRNA expression profiling: a molecular tool for defining the phenotype of hepatocellular tumors, Hepatology, (2008), 47:1807-1809.
Calin et al, MiRNA signature in human cancer, Nat Rev Cancer, (2006), 6:857-866.
Cortez et al, MiRNA identification in plasma and serum: a new tool to diagnose and monitor diseases, Expert Opin Biol Ther, (2009), 9:703-711.
Datta et al, Methylation mediated silencing of miRNA-1 gene and its role in hepatocellular carcinogenesis, Cancer Res, (2008), 68:5049-5058.
Di Bisceglie et al, Serum alpha-fetoprotein levels in patients with advanced hepatitis C: results from the HALT-C trial, J Hepatol, (2005), 43:434-441.
El-Serag et al, Hepatocellular carcinoma: epidemiology and molecular carcinogenesis, Gastroenterology, (2007), 132:2557-2576.
Esquela-Kerscher et al, OncomiRs—microRNA with a role in cancer, Nat Rev Cancer, (2006), 6:259-269.
Filipowicz et al, Mechanisms of post-transcriptional regulation by miRNAs: are the answers in sight? Nat Rev Genet, (2008), 9:102-114.
Fornari et al, MiR-221 control CDKN1C/p57 and CDKN1b/p27 expression in human hepatocellular carcinoma, Oncogene, (2008), 27:5651-5661.
Gomaa et al., Diagnosis of hepatocellular carcinoma, World J Gastroenterol 15(11):1301-1314, (2009).
Gramantieri et al, Cyclin G1 is a target of miR-122a, a miRNA frequently down-regulated in human hepatocellular carcinoma, Cancer Res, (2007), 67:6092-6099.
Gramantieri et al, MiRNA involvement in hepatocellular carcinoma, J Cell Mol Med, (2008), 12:2189-2204.
Guo et al, Effects of upregulated expression of miRNA-16 on biological properties of culture-activated hepatic stellate cells, Apoptosis, Sep. 26, 2009 [Epub ahead of print].
Guo et al, miR-15b and miR-16 are implicated in activation of the rat hepatic stellate cell: an essential role for apoptosis, J Hepatol, (2009), 50:766-778.
Huang et al, Microarray analysis of miRNA expression in hepatocellular carcinoma and non-tumorous tissue without viral hepatitis, J Gastroenterol Hepatol, (2008), 23:87-94.
Ikoma et al., Early Diagnosis of Hepatocellular Carcinoma Using a Sensitive Assay for Serum Des-γ-Carboxy Prothrombin: a Prospective Study, Hepatogastro-enterology. 49:235-238, (2002).
Jiang et al, Association of miRNA expression in hepatocellular carcinomas with hepatitis infection, cirrhosis, and patient survival, Clin Cancer Res, (2008), 14:419-427.
Kim et al, MiRNA miR-199a* regulates the MET proto-oncogene and the downstream extracellular signal-regulated kinase 2 (ERK2), J Biol Chem, (2008), 283:18158-18166.
Kloosterman et al, The diverse functions of miRNA in animal development and disease, Dev Cell, (2006), 11:441-450.
Ladeiro et al, MiRNA profiling in hepatocellular tumors is associated with clinical features and oncogene/tumor suppressor gene mutations, Hepatology, (2008), 47:1955-1963.
Lee et al, MiRNAs in cancer, Annu Rev Pathol, (2009), 4:199-227.
Li et al, Comparison of miRNA expression patterns using total RNA extracted from matched samples of formalin-fixed paraffin-embedded (FFPE) cells and snap frozen cells, BMC Biotechnol, (2007), 7:36.
Lok et al, α-Fetoprotein Monitoring in Chinese Patients with Chronic Hepatitis B Virus Infection: Role in the Early Detection of Hepatocellular Carcinoma, Hepatology, (1989), 9:110-115.
Lu et al, MiRNA expression profiles classify human cancers, Nature, (2005), 435:834-838.
Medina et al, MiRNAs 221 and 222 bypass quiescence and compromise cell survival, Cancer Res, (2008), 68:2773-2780.
Meng et al, MiRNA-21 regulates expression of the PTEN tumor suppressor gene in human hepatocellular cancer, Gastroenterology, (2007), 133:647-658.
Mitchell et al, Circulating miRNAs as stable blood-based markers for cancer detection, Proc Natl Acad Sci USA, (2008), 105:10513-10518.
Miyaaki et al., Lens culinaris agglutinin-reactive α-fetoprotein and protein induced by vitamin K absence II are potential indicators of a poor prognosis: a histopathological study of surgically resected hepatocellular carcinoma, J Gastroenterol. 42:962-968 (2007).
Murakami et al, Comprehensive analysis of miRNA expression pattern in hepatocellular carcinoma and non-tumorous tissues, Oncogene, (2006), 25:2537-2545.
Oka et al., Hepatocellular Carcinoma and a-Fetoprotein, Multicenter prospective analysis of newly diagnosed hepatocellular carcinoma with respect to the percentage of Lens culinaris agglutinin-reactive a-fetoprotein, J Gastroenterol Hepatology 16:1378-1383 (2001).
Pei et al, An overview of hepatocellular carcinoma study by omics-based methods, Acta Biochimica et Biophysica Sinica, (2009), 41:1-15.
Qu, et al, Circulating microRNAa as biomarkers for hepatocellular carcinoma, J Clin Gastroenterol, (2011), 45:355-360.
Shiraki et al., A Clinical Study of Lectin-Reactive Alpha-Fetoprotein as an Early Indicator of Hepatocellular Carcinoma in the Follow-Up of Cirrhotic Patients, Hepatology 22:802-807 (1995).
Toyoda et al, Prognostic Significance of Simultaneous Measurement of Three Tumor Markers in Patients With Hepatocellular Carcinoma, Clinic Gastroenterol Hepatol, 4:111-117, (2006).
Volinia et al, A miRNA expression signature of human solid tumors defines cancer gene target, PNAS USA, (2006), 103:2257-2261.
Volk et al., Risk factors for hepatocellular carcinoma may impair the performance of biomarkers: A comparison of AFP, DCP, and AFP-L3, Cancer Biomark, 3:79-87, (2007).
Xu et al, MiRNA-195 suppresses tumorigenicity and regulates $G_1$/S transition of human hepatocellular carcinoma cells, Hepatology, (2009), 50:113-121.
Yoshida et al., Clinical significance of lens culinaris agglutinin-reactive fraction of serum α-fetoprotein in patients with hepatocellular carcinoma, International J of Oncol. 20:305-309 (2002).
Yuen et al, Screening for hepatocellular carcinoma: survival benefit and cost-effectiveness, Ann Oncol, (2003), 14:1463-1467.
Yuen et al, Serological markers of liver cancer, Best Prac Res Clin Gastroenterol, (2005), 19:91-99.

* cited by examiner

CIRCULATING MICRORNA AS A MARKER FOR HEPATOCELLULAR CARCINOMA

CROSS-REFERENCE TO RELATED APPLICATIONS

This application claims benefit of U.S. Provisional Application 61/313,677, filed Mar. 12, 2010, which is herein incorporated by reference in its entirety.

FIELD OF THE INVENTION

The invention generally relates to the diagnosis, prognosis, and/or management of liver diseases including hepatocellular carcinoma.

BACKGROUND OF THE INVENTION

The following discussion of the background of the invention is merely provided to aid the reader in understanding the invention and is not admitted to describe or constitute prior art to the present invention.

Hepatocellular carcinoma (HCC), the fifth most common solid tumor in the world, has shown a rising trend in terms of both incidence and mortality in the United States. These increases are largely associated with cirrhosis due to chronic hepatitis B virus (HBV) and hepatitis C virus (HCV) infection, alcohol abuse, and other causes. Current diagnosis of HCC in patients with clinical suspicion is based on imaging technology, serum alpha-fetoprotein (AFP) levels, and histology. These diagnostic tools have variable effectiveness for early diagnosis of HCC; cross-sectional imaging typically detects only tumors greater than 1 cm in diameter, and serological studies also lack sensitivity and specificity in patients with small tumors. Consequently, most cases of HCC are diagnosed in an advanced state when treatment options are limited.

MicroRNAs (miRNAs) are non-coding RNAs of 19-25 nucleotides in length that regulate gene expression by inducing translational inhibition or cleavage of their target mRNA through base pairing to partially or fully complementary sites. The miRNAs are involved in important biological processes, including development, cell differentiation, apoptosis and proliferation. miRNAs are also aberrantly expressed in several cancers, suggesting that they may have both oncogenic and tumor suppressor activities.

SUMMARY OF THE INVENTION

The present invention is based on the discovery that circulating miRNA may be detected in patient samples and that the levels of certain miRNA species can have clinical value in the diagnosis, prognosis, and management of liver disease including HCC.

In one aspect, the invention provides methods for diagnosing hepatocellular carcinoma in a subject, the method comprising: determining, in an body fluid sample (e.g., cellular or acellular body fluid) from the subject, the level of one or more miRNAs selected from the group consisting of: miR-16, miR-195, and miR-199a, and diagnosing the subject as having hepatocellular carcinoma when a difference in the level of the one or more miRNAs compared to a reference level indicates hepatocellular carcinoma in the subject. In another aspect, the invention provides methods for determining the prognosis of an individual diagnosed as having hepatocellular carcinoma, wherein the level of one of the foregoing miRNAs in the individual is compared to one or more reference levels determined from patients diagnosed as having hepatocellular carcinoma in which a clinical outcome (i.e., good outcome or poor outcome) is known. The level of any of the foregoing miRNAs are measured and optionally normalized to a internal RNA control (e.g., measured from the same body fluid sample as used to measure the miRNA).

In one embodiment, the reference level is the level in a comparable sample from one or more healthy individuals or one or more chronic liver disease patients. In one embodiment, the one or more miRNAs is compared to a cutoff value determined from the level of one or more miRNAs present in a comparable sample from healthy individuals or from one or more chronic liver disease patients, and wherein an increase or decrease in the subject value relative to the cutoff value is used to determine a diagnosis for the subject.

In one embodiment, the one or more miRNAs is miR-16, and a decreased level in the subject compared to a reference level of one or more healthy individuals one or more chronic liver disease patients indicates a diagnosis of HCC in the subject. For instance, a $\Delta Ct$ value of about 6 or greater for miR-16 indicates a diagnosis of HCC in the subject, wherein the $\Delta Ct$ is the difference between the miR-16 target and an internal control RNA. In one embodiment, the one or more miRNAs is miR-199a, and a decreased level of miR-199a in the subject compared to a reference level of one or more healthy individuals indicates a diagnosis of HCC in the subject. For example, a $\Delta Ct$ value of about 10 or greater for miR-199a indicates a diagnosis of HCC in the subject, wherein the $\Delta Ct$ is the difference between the miR-199a target and an internal control RNA.

In another aspect, the invention provides methods for monitoring the effectiveness of an anti-cancer therapy (e.g., chemotherapy, radiation therapy, and/or surgical resection) in a patient diagnosed as having hepatocellular carcinoma. The level of any of the foregoing miRNAs are measured and optionally normalized to an internal RNA control. In one embodiment, the miRNA level is measured (i) prior to initiating anti-cancer therapy and (ii) after anti-cancer therapy has been initiated. The miRNA levels are compared as an indicator of the effectiveness of the anti-cancer therapy, wherein an increase in the miRNA level following the initiation of anti-cancer therapy indicates that the therapy is effective and no change or a reduction in the miRNA levels following the initiation of therapy indicates that the therapy was ineffective. In another embodiment, the miRNA level is measured after anti-cancer therapy has been initiated and the miRNA level is compared against at least one of (i) a reference level of one or more healthy individuals or one or more chronic liver disease patients.

In one embodiment of any of the foregoing aspects, the acellular body fluid is selected from the group consisting of serum and plasma.

In one embodiment of any of the foregoing aspects, the diagnostic assay further comprises assaying the amount of one or more of α-fetoprotein (AFP), AFP-L3%, and des-gamma-carboxyprothrombin (DCP) in the sample. In an illustrative embodiment, the level of miR-16, AFP, AFP-L3%, and DCP are all determined in the sample. The same sample can be used to measure miRNA and any of AFP, AFP-L3%, or DCP, or different samples from the individual can be used.

In one aspect, the present invention provides a method of diagnosing HCC in a subject, the method comprising: (a) assaying the amount of one or more miRNAs selected from the group consisting of: miR-16 and miR-199a in a test sample from a subject; (b) assaying the amount of one or more of AFP, AFP-L3%, and DCP in the test sample from the subject; (c) determining a score for the subject based on the results obtained in steps (a) and (b); and (d) comparing the score to a cut-off value in order to determine the presence of HCC in the subject. In an illustrative embodiment, the amount of each of the miR-16, AFP, AFP-L3%, and DCP are all assayed in the method.

DETAILED DESCRIPTION OF THE INVENTION

Figure 1:
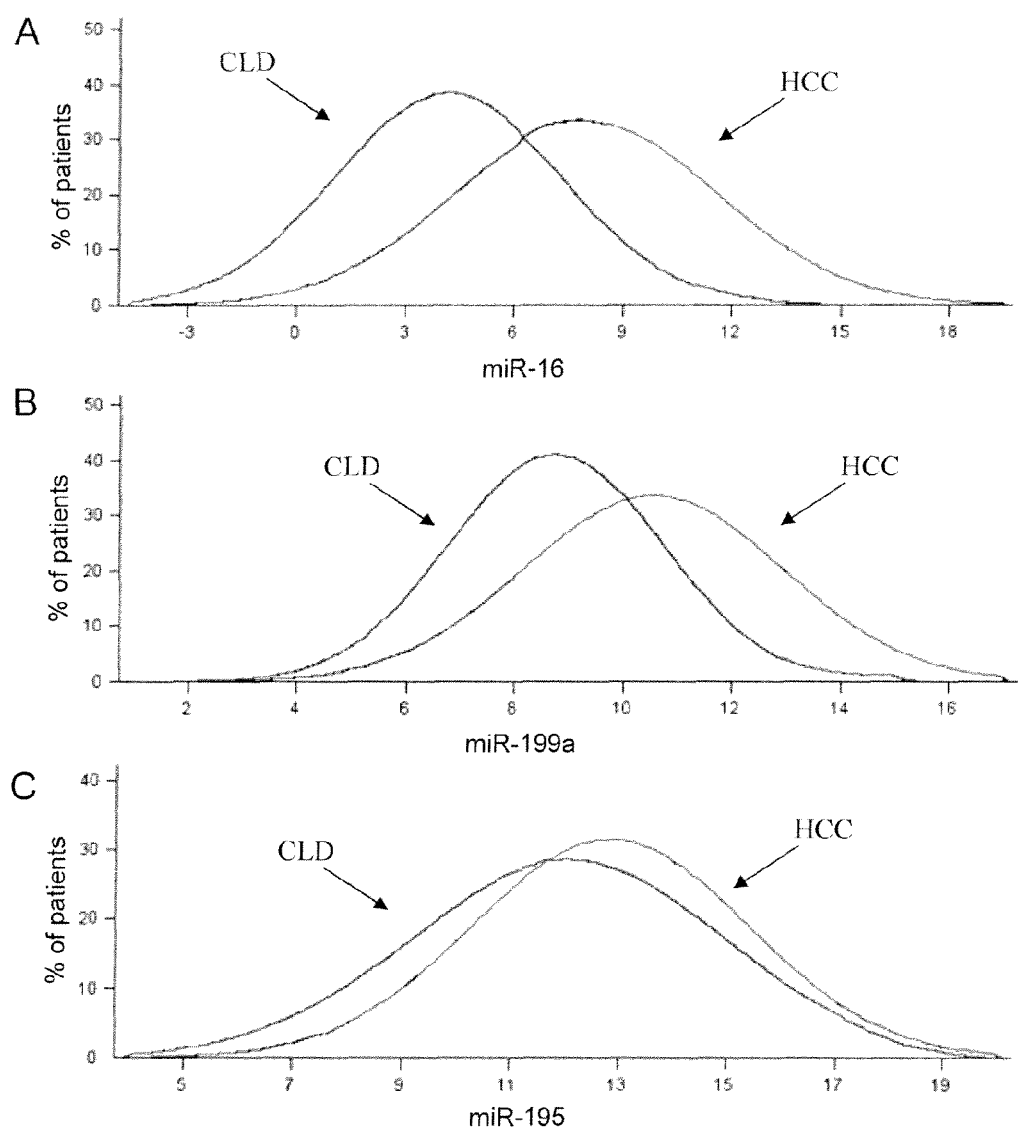
FIG. 1 is a series of graphs showing the distribution of miRNA concentrations in patients with HCC and chronic liver diseases (CLD). A) miR-16; B) miR-199a; C) miR-195. x-axis indicates ΔCt, the difference in cycle threshold (Ct) between the target miRNA and an internal control (small nuclear RNA U6).
Figure 2:
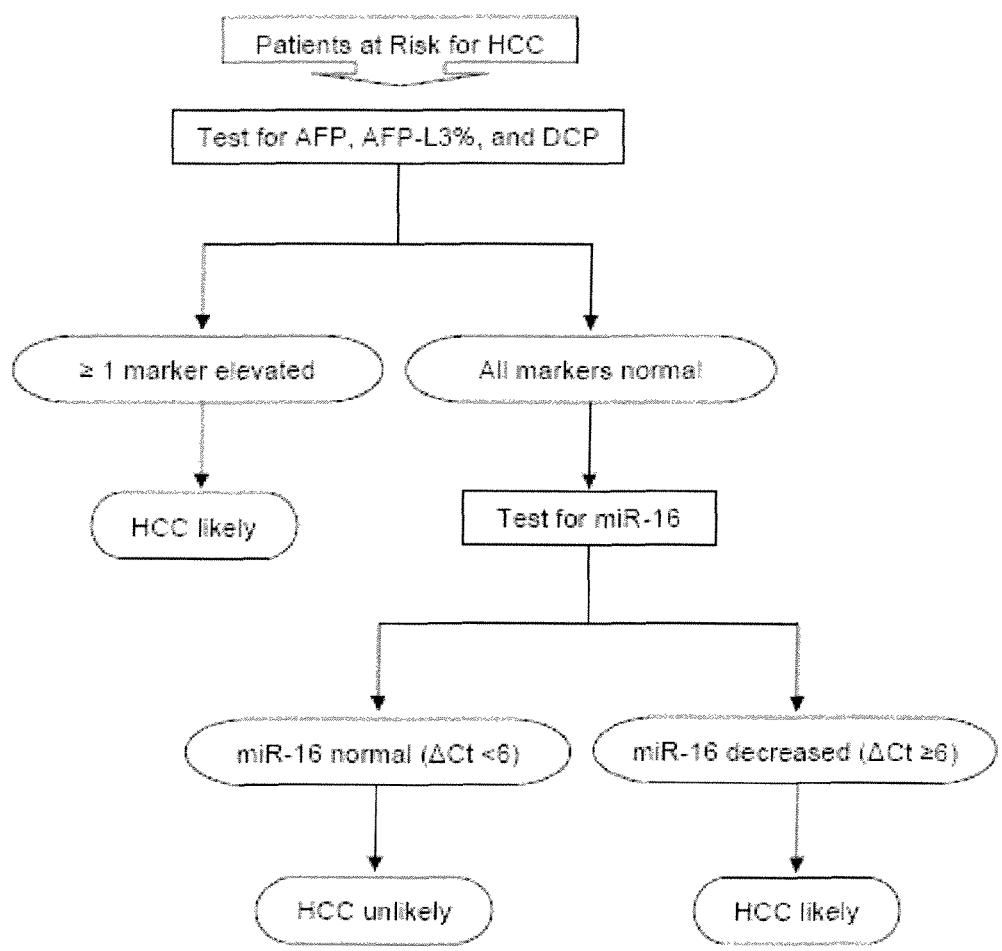
FIG. 2 is a flow chart of an illustrative process for the diagnosis of HCC using biomarkers according to the methods described herein.

The expression of miRNAs may be up-regulated or down-regulated in HCC tumor tissue, relative the corresponding normal tissues. Aberrantly expressed miRNAs could be linked to HCC-associated pathways, indicating a role in liver tumorigenesis that includes promoting cell cycle progression, reducing cell death, and favoring angiogenesis and invasion. The present inventors have discovered that miRNA profiling of body fluids is a powerful tool to differentiate HCC from non-tumorous CLD. The use of circulating miRNAs—alone or in combination with the conventional serum HCC markers AFP, AFP-L3%, and DCP—was investigated to improve differentiation of HCC and CLD.

The present invention relates generally to methods of assessing the circulating miRNAs for the diagnosis of disease. As demonstrated herein, increasing or decreasing amounts of one or more circulating miRNAs correlates with the presence of a disease or the prognosis of a patient suffering from a disease. In particular, methods for diagnosing HCC, determining the likelihood of survival, and methods for predicting likelihood for responsiveness to therapy are provided. Accordingly, various aspects relate to the collection, preparation, separation, identification, characterization, and comparison of the abundance of miRNA and other HCC biomarkers in a test sample. The technology further relates to detecting and/or monitoring a sample containing one or more miRNAs, which are useful, alone or in combination, to determine the presence or absence of a liver disease, such as HCC, or any progressive state thereof including responsiveness to therapy The present technology is described herein using several definitions, as set forth throughout the specification. As used herein, unless otherwise stated, the singular forms "a," "an," and "the" include plural reference. Thus, for example, a reference to "a nucleic acid" is a reference to one or more nucleic acids.

As used herein, "about" will be understood by persons of ordinary skill in the art and will vary to some extent depending upon the context in which it is used. If there are uses of the term which are not clear to persons of ordinary skill in the art, given the context in which it is used, the term "about" in reference to quantitative measurements or values will mean up to plus or minus 10% of the enumerated value.

The term "amplification" or "amplify" as used herein means one or more methods known in the art for copying a target nucleic acid, thereby increasing the number of copies of a selected nucleic acid sequence. Amplification may be exponential or linear. A target nucleic acid may be either DNA or RNA. The sequences amplified in this manner form an "amplicon." While the exemplary methods described hereinafter relate to amplification using the polymerase chain reaction ("PCR"), numerous other methods are known in the art for amplification of nucleic acids (e.g., isothermal methods, rolling circle methods, etc.). The skilled artisan will understand that these other methods may be used either in place of, or together with, PCR methods. See, e.g., Saiki, "Amplification of Genomic DNA" in *PCR Protocols*, Innis et al., Eds., Academic Press, San Diego, Calif. 1990, pp. 13-20; Wharam et al., *Nucleic Acids Res.,* 2001, 29(1):E54-E54; Hafner et al., *Biotechniques* 2001, 30(4):852-6, 858, 860; Zhong et al., *Biotechniques,* 2001, 30(4):852-6, 858, 860.

The terms "determining," "measuring," "assessing," and "assaying" are used interchangeably and include both quantitative and qualitative measurement, and include determining if a characteristic, trait, or feature is present or not. Assessing may be relative or absolute. "Assessing the presence of" includes determining the amount of something present, as well as determining whether it is present or absent.

The term "body fluid" or "bodily fluid" as used herein refers to any fluid from the body of an animal. Examples of body fluids include, but are not limited to, plasma, serum, blood, lymphatic fluid, cerebrospinal fluid, synovial fluid, urine, saliva, mucous, phlegm and sputum. A body fluid sample may be collected by any suitable method. The body fluid sample may be used immediately or may be stored for later use. Any suitable storage method known in the art may be used to store the body fluid sample: for example, the sample may be frozen at about −20° C. to about −70° C. Suitable body fluids are acellular fluids. "Acellular" fluids include body fluid samples in which cells are absent or are present in such low amounts that the miRNA level determined reflects its level in the liquid portion of the sample, rather than in the cellular portion. Such acellular body fluids are generally produced by processing a cell-containing body fluid by, for example, centrifugation or filtration, to remove the cells. Typically, an acellular body fluid contains no intact cells however, some may contain cell fragments or cellular debris. Examples of acellular fluids include plasma or serum, or body fluids from which cells have been removed.

The term "clinical factors" as used herein, refers to any data that a medical practitioner may consider in determining a diagnosis or prognosis of disease. Such factors include, but are not limited to, the patient's medical history, a physical examination of the patient, complete blood count, analysis of the activity of enzymes (e.g., liver enzymes), examination of blood cells or bone marrow cells, cytogenetics, and immunophenotyping of blood cells.

The term "comparable" or "corresponding" in the context of comparing two or more samples, means that the same type of sample (e.g., plasma) is used in the comparison. For example, a level of one or more miRNAs in a sample of plasma can be compared to a level of one or more miRNAs in another plasma sample. In some embodiments, comparable samples may be obtained from the same individual at different times. In other embodiments, comparable samples may be obtained from different individuals (e.g., a patient and a healthy individual). In general, comparable samples are normalized by a common factor. For example, acellular body fluid samples are typically normalized by volume body fluid and cell-containing samples are normalized by protein content or cell count.

The term "complement" as used herein means the complementary sequence to a nucleic acid according to standard Watson/Crick base pairing rules. A complement sequence can also be a sequence of RNA complementary to the DNA sequence or its complement sequence, and can also be a cDNA. The term "substantially complementary" as used herein means that two sequences hybridize under stringent hybridization conditions. The skilled artisan will understand that substantially complementary sequences need not hybridize along their entire length. In particular, substantially complementary sequences comprise a contiguous sequence of bases that do not hybridize to a target or marker sequence, positioned 3' or 5' to a contiguous sequence of bases that hybridize under stringent hybridization conditions to a target or marker sequence.

The phrase "cut-off value" as used herein refers to a diagnostic score that is statistically predictive of a symptom or disease or lack thereof.

As used herein, the term "diagnosis" means detecting a disease or disorder or determining the stage or degree of a disease or disorder. Usually, a diagnosis of a disease or disorder is based on the evaluation of one or more factors and/or symptoms that are indicative of the disease. That is, a diagnosis can be made based on the presence, absence or amount of a factor which is indicative of presence or absence of the disease or condition. Each factor or symptom that is considered to be indicative for the diagnosis of a particular disease does not need be exclusively related to the particular disease; i.e. there may be differential diagnoses that can be inferred from a diagnostic factor or symptom. Likewise, there may be instances where a factor or symptom that is indicative of a particular disease is present in an individual that does not have the particular disease. The diagnostic methods may be used independently, or in combination with other diagnosing and/or staging methods known in the medical art for a particular disease or disorder, e.g., HCC.

As used herein, the phrase "difference of the level" refers to differences in the quantity of a particular marker, such as a nucleic acid or a protein, in a sample as compared to a control or reference level. For example, the quantity of a particular biomarker may be present at an elevated amount or at a decreased amount in samples of patients with a neoplastic disease compared to a reference level. In one embodiment, a "difference of a level" may be a difference between the quantity of a particular biomarker present in a sample as compared to a control of at least about 1%, at least about 2%, at least about 3%, at least about 5%, at least about 10%, at least about 15%, at least about 20%, at least about 25%, at least about 30%, at least about 35%, at least about 40%, at least about 50%, at least about 60%, at least about 75%, at least about 80% or more. In one embodiment, a "difference of a level" may be a statistically significant difference between the quantity of a biomarker present in a sample as compared to a control. For example, a difference may be statistically significant if the measured level of the biomarker falls outside of about 1.0 standard deviations, about 1.5 standard deviations, about 2.0 standard deviations, or about 2.5 stand deviations of the mean of any control or reference group. With respect to miRNA measurement, the level may be measured from real-time PCR as the Ct value, which may be normalized to a ΔCt value as described in the Examples.

By "isolated", when referring to a nucleic acid (e.g., an oligonucleotide such as RNA, DNA, or a mixed polymer) is meant a nucleic acid that is apart from a substantial portion of the genome in which it naturally occurs and/or is substantially separated from other cellular components which naturally accompany such nucleic acid. For example, any nucleic acid that has been produced synthetically (e.g., by serial base condensation) is considered to be isolated. Likewise, nucleic acids that are recombinantly expressed, cloned, produced by a primer extension reaction (e.g., PCR), or otherwise excised from a genome are also considered to be isolated.

The term "enzyme linked immunosorbent assay" (ELISA) as used herein refers to an antibody-based assay in which detection of the antigen of interest is accomplished via an enzymatic reaction producing a detectable signal. ELISA can be run as a competitive or non-competitive format. ELISA also includes a 2-site or "sandwich" assay in which two antibodies to the antigen are used, one antibody to capture the antigen and one labeled with an enzyme or other detectable label to detect captured antibody-antigen complex. In a typical 2-site ELISA, the antigen has at least one epitope to which unlabeled antibody and an enzyme-linked antibody can bind with high affinity. An antigen can thus be affinity captured and detected using an enzyme-linked antibody. Typical enzymes of choice include alkaline phosphatase or horseradish peroxidase, both of which generated a detectable product upon digestion of appropriate substrates.

The term "label" as used herein, refers to any physical molecule directly or indirectly associated with a specific binding agent or antigen which provides a means for detection for that antibody or antigen. A "detectable label" as used herein refers any moiety used to achieve signal to measure the amount of complex formation between a target and a binding agent. These labels are detectable by spectroscopic, photochemical, biochemical, immunochemical, electromagnetic, radiochemical, or chemical means, such as fluorescence, chemifluorescence, or chemiluminescence, electrochemiluminescence or any other appropriate means. Suitable detectable labels include fluorescent dye molecules or fluorophores.

The term "liver disease" refers to and comprises all kinds of disorders that affect the anatomy, physiology, metabolism, and/or genetic activities of the liver, that affect the generation of new liver cells and/or the regeneration of the liver, as a whole or parts thereof, transiently, temporarily, chronically or permanently, in a pathological way. In some embodiments, the liver disease is caused by alcohol (e.g. ASH), non-alcoholic fatty liver changes (such as NAFLD including NASH), nutrition-mediated liver injury, other toxic liver injury (such as unspecific hepatitis induced by e.g. drugs such as but not limited to acetaminophen (paracetamol), chlorinated hydrocarbons (e.g. $CCl_4$), amiodarone (cordarone), valproate, tetracycline, isoniacid, or food intoxication resulting in acute or chronic liver failure, e.g. by consumption of mushrooms containing aflatoxins or ingestion of certain metals (such as copper or cadmium) or herbal products used in natural medicine (homeopathics such as Milk thistle, Chaparral, Kawa-Kawa), interference of bilirubin metabolism, hepatitis like syndromes, cholestasis, granulomatous lesions, intrahepatic vascular lesions and cirrhosis), trauma and surgery, and radiation-mediated liver injury (such as caused by radiotherapy). In one embodiment, the liver disease is caused by an infection, e.g., by hepatitis B virus (HBV) and hepatitis C virus (HCV) infections, and autoimmune-mediated liver disease (e.g. autoimmune hepatitis). Further included is liver injury due to sepsis. In some embodiment, liver disease is further understood to comprise genetic liver disorders (such as hemachromatosis and alpha1 antitrypsin deficiency), and other inherited metabolic liver diseases, e.g. metabolic steatohepatitis (MSH).

As used herein interchangeably, a "microRNA," "miR," or "miRNA" refers to the unprocessed or processed RNA transcript from a miRNA gene. The unprocessed miRNA gene transcript is also called a "miRNA precursor," and typically comprises an RNA transcript of about 70-100 nucleotides in length. The miRNA precursor can be processed by digestion with an RNAse (for example, Dicer, Argonaut, or RNAse III) into an active 19-25 nucleotide RNA molecule. This active 19-25 nucleotide RNA molecule is also called the "processed" miRNA gene transcript or "mature" miRNA.

The term "neoplastic diseases" as used herein refers to cancers of any kind and origin and precursor stages thereof. Accordingly, the term "neoplastic disease" includes the subject matter identified by the terms "neoplasia", "neoplasm", "cancer", "pre-cancer" or "tumor". A neoplastic disease is generally manifest by abnormal cell division resulting in an abnormal level of a particular cell population. The abnormal cell division underlying a neoplastic disease is typically inherent in the cells and not a normal physiological response to infection or inflammation. In some embodiments, neoplastic diseases for diagnosis using methods provided herein include carcinoma. By "carcinoma," it is meant a benign or malignant epithelial tumor and includes, but is not limited to, hepatocellular carcinoma, breast carcinoma, prostate carcinoma, non-small cell lung carcinoma, colon carcinoma, CNS carcinoma, melanoma, ovarian carcinoma, or renal carcinoma. An exemplary neoplastic disease is hepatocellular carcinoma.

As used herein, "nucleic acid" refers broadly to segments of a chromosome, segments or portions of DNA, cDNA, and/or RNA. Nucleic acid may be derived or obtained from an originally isolated nucleic acid sample from any source (e.g., isolated from, purified from, amplified from, cloned from, or reverse transcribed from sample DNA or RNA).

As used herein, the term "oligonucleotide" refers to a short polymer composed of deoxyribonucleotides, ribonucleotides or any combination thereof. Oligonucleotides are generally between about 10 and about 100 nucleotides in length. Oligonucleotides are typically 15 to 70 nucleotides long, with 20 to 26 nucleotides being the most common. An oligonucleotide may be used as a primer or as a probe.

An oligonucleotide is "specific" for a nucleic acid if the oligonucleotide has at least 50% sequence identity with a portion of the nucleic acid when the oligonucleotide and the nucleic acid are aligned. An oligonucleotide that is specific for a nucleic acid is one that, under the appropriate hybridization or washing conditions, is capable of hybridizing to the target of interest and not substantially hybridizing to nucleic acids which are not of interest. Higher levels of sequence identity are preferred and include at least 75%, at least 80%, at least 85%, at least 90%, or at least 95% sequence identity.

As used herein, a "primer" for amplification is an oligonucleotide that specifically anneals to a target or marker nucleotide sequence. The 3' nucleotide of the primer should be identical to the target or marker sequence at a corresponding nucleotide position for optimal primer extension by a polymerase. As used herein, a "forward primer" is a primer that anneals to the anti-sense strand of double stranded DNA (dsDNA). A "reverse primer" anneals to the sense-strand of dsDNA.

The term "prognosis" as used herein refers to a prediction of the probable course and outcome of a clinical condition or disease. A prognosis is usually made by evaluating factors or symptoms of a disease that are indicative of a favorable or unfavorable course or outcome of the disease. The phrase "determining the prognosis" as used herein refers to the process by which the skilled artisan can predict the course or outcome of a condition in a patient. The term "prognosis" does not refer to the ability to predict the course or outcome of a condition with 100% accuracy instead, the skilled artisan will understand that the term "prognosis" refers to an increased probability that a certain course or outcome will occur; that is, that a course or outcome is more likely to occur in a patient exhibiting a given condition, when compared to those individuals not exhibiting the condition.

The terms "favorable prognosis" and "positive prognosis," or "unfavorable prognosis" and "negative prognosis" as used herein are relative terms for the prediction of the probable course and/or likely outcome of a condition or a disease. A favorable or positive prognosis predicts a better outcome for a condition than an unfavorable or negative prognosis. In a general sense, a "favorable prognosis" is an outcome that is relatively better than many other possible prognoses that could be associated with a particular condition, whereas an unfavorable prognosis predicts an outcome that is relatively worse than many other possible prognoses that could be associated with a particular condition. Typical examples of a favorable or positive prognosis include a better than average cure rate, a lower propensity for metastasis, a longer than expected life expectancy, differentiation of a benign process from a cancerous process, and the like. For example, a positive prognosis is one where a patient has a 50% probability of being cured of a particular cancer after treatment, while the average patient with the same cancer has only a 25% probability of being cured.

As used herein, "plasma" refers to acellular fluid found in blood. Plasma may be obtained from blood by removing whole cellular material from blood by methods known in the art (e.g., centrifugation, filtration, and the like). As used herein, "peripheral blood plasma" refers to plasma obtained from peripheral blood samples. As used herein, "serum" includes the fraction of plasma obtained after plasma or blood is permitted to clot and the clotted fraction is removed.

The terms "polypeptide," "protein," and "peptide" are used herein interchangeably to refer to amino acid chains in which the amino acid residues are linked by peptide bonds or modified peptide bonds. The amino acid chains can be of any length of greater than two amino acids. Unless otherwise specified, the terms "polypeptide," "protein," and "peptide" also encompass various modified forms thereof. Such modified forms may be naturally occurring modified forms or chemically modified forms. Examples of modified forms include, but are not limited to, glycosylated forms, phosphorylated forms, myristoylated forms, palmitoylated forms, ribosylated forms, acetylated forms, ubiquitinated forms, etc. Modifications also include intra-molecular crosslinking and covalent attachment to various moieties such as lipids, flavin, biotin, polyethylene glycol or derivatives thereof, etc. In addition, modifications may also include cyclization, branching and cross-linking. Further, amino acids other than the conventional twenty amino acids encoded by genes may also be included in a polypeptide.

As used herein, the term "reference level" refers to a level of a substance which may be of interest for comparative purposes. In one embodiment, a reference level may be one or more circulating miRNA levels expressed as an average of the level of the circulating miRNA from samples taken from a control population of healthy (disease-free) subjects. In another embodiment, the reference level may be the level in the same subject at a different time, e.g., before the present assay, such as the level determined prior to the subject developing the disease or prior to initiating therapy. In general, samples are normalized by a common factor. For example, acellular body fluid samples are normalized by volume body fluid and cell-containing samples are normalized by protein content or cell count. Nucleic acid samples may also be normalized relative to an internal control nucleic acid.

As used herein, the term "sample" may include, but is not limited to, bodily tissue or a bodily fluid such as blood (or a fraction of blood such as plasma or serum), lymph, mucus, tears, saliva, sputum, urine, semen, stool, CSF, ascites fluid, or whole blood, and including biopsy samples of body tissue. A sample may be obtained from any subject, e.g., a subject/patient having or suspected to have a neoplastic disease.

As used herein, the term "subject" refers to a mammal, such as a human, but can also be another animal such as a domestic animal (e.g., a dog, cat, or the like), a farm animal (e.g., a cow, a sheep, a pig, a horse, or the like) or a laboratory animal (e.g., a monkey, a rat, a mouse, a rabbit, a guinea pig, or the like). The term "patient" refers to a subject who is, or is suspected to be, afflicted with HCC.

The phrase "substantially the same as" in reference to a comparison of one value to another value for the purposes of clinical management of a disease or disorder means that the values are statistically not different. Differences between the values can vary, for example, one value may be within 20%, within 10%, or within 5% of the other value.

As used herein, the term "diagnostic score" refers to a single number or score, based on a statistical analysis of the measured level of one or more biomarkers that reflects a relationship of a specific subject to any one particular group of individuals, such as normal individuals or individuals having a disease or any progressive state thereof. In some embodiments, the diagnostic score is derived from a quantitative multivariate analysis, which reflects the overall statistical assessment of an individual patient's clinical condition based upon an integrated statistical calculation of a plurality of qualitatively unique factors, e.g., levels of serum miR-16, miR-199a, AFP, AFP-L3%, and/or DCP, age, gender, etc.

Overview

Disclosed herein are methods for detecting the presence or absence of HCC in subjects based, at least in part, on results of testing assays on a sample. Further disclosed herein are methods for monitoring the status of subjects diagnosed with HCC and/or chronic liver disease based at least partially on results of tests on a sample. The test samples disclosed herein are represented by, but not limited in anyway to, sputum, blood (or a fraction of blood such as plasma, serum, or particular cell fractions), lymph, mucus, tears, saliva, urine, semen, ascites fluid, whole blood, and biopsy samples of body tissue. This disclosure is drawn, inter alia, to methods of diagnosing and monitoring liver diseases using profiles of miRNA in acellular body fluid samples.

Biopsy is considered the gold standard for assessment of liver disease, but it is an invasive procedure that carries the risk of complications. Moreover, biopsy can yield misleading results when a representative sample is not obtained. Alternative tests that are simple, reliable, and non-invasive would thus be of benefit in the diagnosis and staging of HCC and/or non-HCC chronic liver disease (CLD). The use of AFP, AFP-L3%, and DCP, alone and in combination, have been investigated for the detection of HCC. However, the reported sensitivity and specificity of each marker vary widely, largely because of differences in the cutoff values used. Moreover, although AFP is currently the most commonly used serum tumor marker for screening HCC, the American Association for the Study of Liver Diseases has recommended against its use as a sole marker for HCC screening unless ultrasonography is not available. The conventional HCC markers usually provide good detection of HCC patients with large tumors, however, early detection of HCC is a key factor for HCC therapeutic response.

The present inventors have established a link between alterations in circulating miRNA levels and HCC. In some embodiments, the level of circulating miRNAs, alone and in combination with conventional HCC serum markers, are used to improve HCC detection. In exemplary embodiments, the miRNAs are selected from the group consisting of: miR-16, miR-199a, and miR-195. In one embodiment, miR-16, combined with AFP, AFP-L3%, and DCP, yields greater sensitivity than the conventional HCC markers alone. In some embodiments, HCC can be diagnosed in patients with tumors≤about 3 cm. As shown in the Examples, miR-16 identified 34 of the 43 (79%) patients with small tumors, a markedly higher frequency than identified with the individual conventional serum markers of HCC. Furthermore, the combination of miR-16 with the three conventional HCC markers increased the sensitivity significantly. In some embodiments, the combination of miR-16 with AFP, AFP-L3%, and DCP yields excellent diagnostic characteristics, with a sensitivity of 92.4% and specificity of 78.5%. Furthermore, miR-16 measurement as a second-line test identified a substantial proportion of HCC cases that exhibited false-negative results with all 3 conventional HCC markers.

In one aspect, the methods generally provide for the detection, measuring, and comparison of a pattern of circulating miRNA in a patient sample. In the context of cancer diagnosis, it is frequently difficult to have access to the diseased cells. In various embodiments, the present methods overcome problems of cancer diagnosis by determining the levels of miRNAs in the plasma of patients with liver diseases. An alteration (i.e., an increase or decrease) in the level of a miRNA gene product in the sample obtained from the subject, relative to the level of a corresponding miRNA gene product in a control sample, is indicative of the presence of HCC in the subject. In one embodiment, the level of at least one miRNA gene product in the test sample is greater than the level of the corresponding miRNA gene product in the control sample. In another embodiment, the level of at least one miRNA gene product in the test sample is less than the level of the corresponding miRNA gene product in the control sample. In one embodiment, serum levels of miR-16 and miR-199a are significantly lower in patients with HCC than that in normal subjects or CLD subjects.

Additional diagnostic markers may be combined with the circulating miRNA level to construct models for predicting the presence or absence or stage of a disease. For example, clinical factors of relevance to the diagnosis of HCC diseases, include, but are not limited to, the patient's medical history, a physical examination, complete blood count, the level of AFP, AFP-L3%, ALT, ALP and AST, and other markers.

Sample Preparation

Test samples of acellular body fluid or cell-containing samples may be obtained from an individual or patient. Methods of obtaining test samples are well-known to those of skill in the art and include, but are not limited to aspirations or drawing of blood or other fluids. Samples may include, but are not limited to, whole blood, serum, plasma, saliva, cerebrospinal fluid (CSF), pericardial fluid, pleural fluid, urine, and eye fluid. In some embodiments in which the test sample contains cells, the cells may be removed from the liquid portion of the sample by methods known in the art (e.g., centrifugation) to yield acellular body fluid. In suitable embodiments, serum or plasma are used as the acellular body fluid sample. Plasma and serum can be prepared from whole blood using suitable methods well-known in the art. In these embodiments, data may be normalized by volume of acellular body fluid.

Variability in sample preparation of cell-containing samples can be corrected by normalizing the data by, for example, protein content or cell number. In certain embodiments, the sample may be normalized relative to the total protein content in the sample. Total protein content in the sample can be determined using standard procedures, including, without limitation, Bradford assay and the Lowry method. In other embodiments, the sample may be normalized relative to cell number.

Nucleic Acid Extraction and Detection

The level of a miRNA gene product in a sample can be measured using any technique that is suitable for detecting RNA expression levels in a biological sample. Suitable techniques for determining RNA expression levels in a biological sample are well known to those of skill in the art. These include, for example, Northern blot analysis, RT-PCR, and in situ hybridization.

The nucleic acid to be detected may be from a biological sample such as a body fluid sample and the like. Various methods of extraction are suitable for isolating the DNA or RNA. Suitable methods include phenol and chloroform extraction. See Maniatis et al. *Molecular Cloning, A Laboratory Manual*, 2d, Cold Spring Harbor Laboratory Press, pp. 16-54 (1989). Numerous commercial kits also yield suitable DNA and RNA including, but not limited to, QIAamp™ mini blood kit, Agencourt Genfind™, Roche Cobas® Roche MagNA Pure® or phenol:chloroform extraction using Eppendorf Phase Lock Gels®, and the NucliSens extraction kit (Biomerieux, Marcy l'Etoile, France). In an illustrative embodiment. RNA is isolated from patient serum on the NucliSens easyMAG system (Biomeriux SA, France) according to the manufacturer's protocol.

In one embodiment, the level of at least one miRNA gene product is detected using Northern blot analysis. For example, total RNA can be purified from a sample in the presence of nucleic acid extraction buffer, followed by centrifugation. Nucleic acids are precipitated, and DNA is removed by treatment with DNase and precipitation. The RNA molecules are then separated by gel electrophoresis on agarose gels according to standard techniques, and transferred to nitrocellulose filters. The RNA is then immobilized on the filters by heating. Detection and quantification of specific RNA is accomplished using appropriately labeled DNA or RNA probes complementary to the RNA in question. See, for example, *Molecular Cloning: A Laboratory Manual*, J. Sambrook et al., eds., 2nd edition, Cold Spring Harbor Laboratory Press, 1989, Chapter 7.

Suitable probes (e.g., DNA probes or RNA probes) for Northern blot hybridization of a given miRNA gene product can be produced from the known nucleic acid sequences and include, but are not limited to, probes having at least about 70%, 75%, 80%, 85%, 90%, 95%, 98% or 99% complementarity to a miRNA gene product of interest, as well as probes that have complete complementarity to a miRNA gene product of interest. Methods for preparation of labeled DNA and RNA probes, and the conditions for hybridization thereof to target nucleotide sequences, are described in *Molecular Cloning: A Laboratory Manual*, J. Sambrook et al., eds., 2nd edition, Cold Spring Harbor Laboratory Press, 1989, Chapters 10 and 11.

For example, the nucleic acid probe can be labeled with, e.g., a radionuclide, such as $^{3}H$, $^{32}P$, $^{33}P$, $^{14}C$, or $^{35}S$; a heavy metal; a ligand capable of functioning as a specific binding pair member for a labeled ligand (e.g., biotin, avidin or an antibody); a fluorescent molecule: a chemiluminescent molecule; an enzyme or the like. Probes can be labeled to high specific activity by either the nick translation method or by the random priming method. Autoradiographic detection of hybridization can then be performed by exposing hybridized filters to photographic film. Densitometric scanning of the photographic films exposed by the hybridized filters provides an accurate measurement of miRNA levels. Using another approach, miRNA gene transcript levels can be quantified by computerized imaging systems.

In one embodiment, the miRNA is detected using a nucleic acid amplification process. Nucleic acid extracted from a sample can be amplified using nucleic acid amplification techniques well known in the art. By way of example, but not by way of limitation, these techniques can include the polymerase chain reaction (PCR), reverse transcriptase polymerase chain reaction (RT-PCR), nested PCR, ligase chain reaction. See Abravaya, K., et al., *Nucleic Acids Research*, 23:675-682, (1995), branched DNA signal amplification, Urdea, M. S., et al., *AIDS*, 7 (suppl 2):S11-S14, (1993), amplifiable RNA reporters, Q-beta replication, transcription-based amplification, boomerang DNA amplification, strand displacement activation, cycling probe technology, isothermal nucleic acid sequence based amplification (NASBA). See Kievits, T. et al., *J Virological Methods*, 35:273-286, (1991), Invader Technology, or other sequence replication assays or signal amplification assays may also be used.

Some methods employ reverse transcription of RNA to cDNA. The method of reverse transcription and amplification may be performed by previously published or recommended procedures. Various reverse transcriptases may be used, including, but not limited to, MMLV RT, RNase H mutants of MMLV RT such as Superscript and Superscript II (Life Technologies, GIBCO BRL, Gaithersburg, Md.), AMV RT, and thermostable reverse transcriptase from *Thermus thermophilus*. For example, one method which may be used to convert RNA to cDNA is the protocol adapted from the Superscript II Preamplification system (Life Technologies, GIBCO BRL, Gaithersburg, Md.; catalog no. 18089-011), as described by Rashtchian, A., *PCR Methods Applic.*, 4:S83-S91, (1994).

In a suitable embodiment, PCR is used to amplify a target sequence of interest. PCR is a technique for making many copies of a specific template DNA sequence. The reaction consists of multiple amplification cycles and is initiated using a pair of primer sequences that hybridize to the 5' and 3' ends of the sequence to be copied. The amplification cycle includes an initial denaturation, and typically up to 50 cycles of annealing, strand elongation and strand separation (denaturation). In each cycle of the reaction, the DNA sequence between the primers is copied. Primers can bind to the copied DNA as well as the original template sequence, so the total number of copies increases exponentially with time. PCR can be performed as according to Whelan et al., *J of Clin Micro*, 33(3):556-561 (1995). Briefly, a PCR reaction mixture includes two specific primers, dNTPs, approximately 0.25 U of Taq polymerase, and 1×PCR Buffer.

The skilled artisan is capable of designing and preparing primers that are appropriate for amplifying a target or marker sequence. The length of the amplification primers depends on several factors including the nucleotide sequence identity and the temperature at which these nucleic acids are hybridized or used during in vitro nucleic acid amplification. The considerations necessary to determine a preferred length for an amplification primer of a particular sequence identity are well-known to a person of ordinary skill. For example, the length of a short nucleic acid or oligonucleotide can relate to its hybridization specificity or selectivity.

In some embodiments, the amplification may include a labeled primer or probe, thereby allowing detection of the amplification products corresponding to that primer or probe. In particular embodiments, the amplification may include a multiplicity of labeled primers or probes; such primers may be distinguishably labeled, allowing the simultaneous detection of multiple amplification products. Oligonucleotide probes can be designed which are between about 10 and about 100 nucleotides in length and hybridize to the amplified region. Oligonucleotides probes are preferably 12 to 70 nucleotides; more preferably 15-60 nucleotides in length; and most preferably 15-25 nucleotides in length. The probe may be labeled.

In one embodiment, a primer or probe is labeled with a fluorogenic reporter dye that emits a detectable signal. While a suitable reporter dye is a fluorescent dye, any reporter dye that can be attached to a detection reagent such as an oligonucleotide probe or primer is suitable for use in the invention. Such dyes include, but are not limited to, Acridine, AMCA, BODIPY, Cascade Blue, Cy2, Cy3, Cy5, Cy7, Edans, Eosin, Erythrosin, Fluorescein, 6-Fam, Tet, Joe, Hex, Oregon Green, Rhodamine, Rhodol Green, Tamra, Rox, and Texas Red.

In yet another embodiment, the detection reagent may be further labeled with a quencher dye such as Tamra, Dabcyl, or Black Hole Quencher® (BHQ), especially when the reagent is used as a self-quenching probe such as a TaqMan® (U.S. Pat. Nos. 5,210,015 and 5,538,848) or Molecular Beacon probe (U.S. Pat. Nos. 5,118,801 and 5,312,728), or other stemless or linear beacon probe (Livak et al., 1995, *PCR Method App.*, 4:357-362; Tyagi et al, 1996, *Nature Biotechnology*, 14:303-308; Nazarenko et al., 1997, *Nucl. Acids Res.*, 25:2516-2521; U.S. Pat. Nos. 5,866,336 and 6,117,635).

Nucleic acids may be amplified prior to detection or may be detected directly during an amplification step (i.e., "real-time" methods). For example, amplified fragments may be detected using standard gel electrophoresis methods. In some embodiments, amplified fractions are separated on an agarose gel and stained with ethidium bromide by methods known in the art to detect amplified fragments. In some embodiments, the target sequence is amplified using a labeled primer such that the resulting amplicon is detectably labeled. In some embodiments, the primer is fluorescently labeled.

In one embodiment, detection of a miRNA, such as a nucleic acid from an a miR-16 or miR-199a, is performed using the TaqMan® assay, which is also known as the 5' nuclease assay (U.S. Pat. Nos. 5,210,015 and 5,538,848). The TaqMan® assay detects the accumulation of a specific amplified product during PCR. The TaqMan® assay utilizes an oligonucleotide probe labeled with a fluorescent reporter dye and a quencher dye. The reporter dye is excited by irradiation at an appropriate wavelength, it transfers energy to the quencher dye in the same probe via a process called fluorescence resonance energy transfer (FRET). When attached to the probe, the excited reporter dye does not emit a signal. The proximity of the quencher dye to the reporter dye in the intact probe maintains a reduced fluorescence for the reporter. The reporter dye and quencher dye may be at the 5' most and the 3' most ends, respectively or vice versa. Alternatively, the reporter dye may be at the 5' or 3' most end while the quencher dye is attached to an internal nucleotide, or vice versa. In yet another embodiment, both the reporter and the quencher may be attached to internal nucleotides at a distance from each other such that fluorescence of the reporter is reduced.

During PCR, the 5' nuclease activity of DNA polymerase cleaves the probe, thereby separating the reporter dye and the quencher dye and resulting in increased fluorescence of the reporter. Accumulation of PCR product is detected directly by monitoring the increase in fluorescence of the reporter dye. The DNA polymerase cleaves the probe between the reporter dye and the quencher dye only if the probe hybridizes to the target-containing template which is amplified during PCR.

TaqMan® primer and probe sequences can readily be determined using the nucleic acid sequence information of the miRNA of interest. A number of computer programs, such as Primer Express (Applied Biosystems, Foster City, Calif.), can be used to rapidly obtain optimal primer/probe sets. It will be apparent to one of skill in the art that such primers and probes for detecting the target nucleic acids are useful in diagnostic assays for neoplastic disorders, such as HCC, and can be readily incorporated into a kit format. The present invention also includes modifications of the TaqMan® assay well known in the art such as the use of Molecular Beacon probes (U.S. Pat. Nos. 5,118,801 and 5,312,728) and other variant formats (U.S. Pat. Nos. 5,866,336 and 6,117,635).

In an illustrative embodiment, real time PCR is performed using TaqMan® Assays in combination with a suitable amplification/analyzer such as the ABI Prism® 7900HT Sequence Detection System. The ABI PRISM® 7900HT Sequence Detection System is a high-throughput real-time PCR system that detects and quantitates nucleic acid sequences. Real-time detection on the ABI Prism 7900HT or 7900HT Sequence Detector monitors fluorescence and calculates Rn during each PCR cycle. The threshold cycle, or Ct value, is the cycle at which fluorescence intersects the threshold value. The threshold value is determined by the sequence detection system software or manually. The Ct can be correlated to the initial amount of nucleic acids or number of starting cells using a standard curve.

In one embodiment, TaqMan® MicroRNA Assays are used to detect the miRNA. TaqMan® MicroRNA Assays are predesigned assays that are available for the majority of content found on the miRBase miRNA sequence repository. In another embodiment, the mirVana™ qRT-PCR miRNA Detection Kit (Ambion) is a used to detect and quantify the miRNA. This is a quantitative reverse transcription-PCR (qRT-PCR) kit enabling sensitive, rapid quantification of miRNA (miRNA) expression from total RNA samples.

As a quality control measure, an internal amplification control may be included in one or more samples to be extracted and amplified. The skilled artisan will understand that any detectable sequence that is not typically present in the sample can be used as the control sequence. A control sequence can be produced synthetically. If PCR amplification is successful, the internal amplification control amplicons can then be detected. Additionally, if included in the sample prior to purification of nucleic acids, the control sequences can also act as a positive purification control.

Diagnosis of Hepatocellular Carcinoma

Provided herein are methods of diagnosing hepatocellular carcinoma (HCC) and differentiating HCC from non-HCC chronic liver disease. Liver cancer is the fifth most common cancer and the third leading cancer killer worldwide, and is responsible for about half million new cases and almost as many deaths per year. HCC is the major histological type of primary liver cancer. Major risk factors for developing HCC include hepatitis B virus (HBV) infection and hepatitis C virus (HCV) infection. The median survival duration is typically less than a year, because the majority of these cancers are unresectable, not suitable for new treatment modalities, and have low chemotherapy response rates. Surgical resection, such as partial hepatectomy or liver transplantation, is the most common curative treatment for the disease. However, only 20% of patients are eligible for surgery because the majority of patients are diagnosed at an advanced stage with intra- and/or extra-hepatic metastases. After curative surgery, recurrence is common and the incidence is about 50% in the first year. Thus, early detection of HCC is essential to improve survival. A diagnostic test for the detection of early-stage cancers in asymptomatic patients is one aspect of the invention.

Association between a pathological state (e.g., HCC) and the aberration of the level of one or more circulating miRNAs can be readily determined by comparative analysis in a normal population and an abnormal or affected population. Thus, for example, one can study the circulating miRNAs in both a normal population and a population affected with a particular pathological state. The study results can be compared and analyzed by statistical means. Any detected statistically significant difference in the two populations would indicate an association. For example, if the level of circulating miRNAs is statistically significantly lower in the affected population than in the normal population, then it can be reasonably concluded that the lower circulating miRNA is associated with the pathological state.

Statistical methods can be used to set thresholds for determining when the level in a subject can be considered to be different than or similar to a reference level. In addition, statistics can be used to determine the validity of the difference or similarity observed between a patient's circulating miRNA level and the reference level. Useful statistical analysis methods are described in L. D. Fisher & G. vanBelle, *Biostatistics: A Methodology for the Health Sciences* (Wiley-Interscience, NY, 1993). For instance, confidence ("p") values can be calculated using an unpaired 2-tailed t test, with a difference between groups deemed significant if the p value is less than or equal to 0.05. As used herein a "confidence interval" or "CI" refers to a measure of the precision of an estimated or calculated value. The interval represents the range of values, consistent with the data that is believed to encompass the "true" value with high probability (usually 95%). The confidence interval is expressed in the same units as the estimate or calculated value. Wider intervals indicate lower precision; narrow intervals indicate greater precision. Preferred confidence intervals of the invention are 90%, 95%, 97.5%, 98%, 99%, 99.5%, 99.9% and 99.99%. A "p-value" as used herein refers to a measure of probability that a difference between groups happened by chance. For example, a difference between two groups having a p-value of 0.01 (or p=0.01) means that there is a 1 in 100 chance the result occurred by chance. Preferred p values are 0.1, 0.05, 0.025, 0.02, 0.01, 0.005, 0.001, and 0.0001. Confidence intervals and p-values can be determined by methods well-known in the art. See, e.g., Dowdy and Wearden, *Statistics for Research*, John Wiley & Sons, New York, 1983.

Once an association is established between a level of one or more circulating miRNA and a pathological state, then the particular physiological state can be diagnosed or detected by determining whether a patient has the particular aberration, i.e. elevated or reduced circulating miRNA levels. The term "elevated levels" or "higher levels" as used herein refers to levels of a circulating miRNA that are higher than what would normally be observed in a comparable sample from control or normal subjects (i.e., a reference value). In some embodiments, "control levels" (i.e., normal levels) refer to a range of circulating miRNA levels that would be normally be expected to be observed in a mammal that does not have a neoplastic disease. A control level may be used as a reference level for comparative purposes. "Elevated levels" refer to circulating miRNA levels that are above the range of control levels. The ranges accepted as "elevated levels" or "control levels" are dependent on a number of factors. For example, one laboratory may routinely determine the level of circulating miRNA in a sample that is different than the circulating miRNA obtained for the same sample by another laboratory. Also, different assay methods may achieve different value ranges. Value ranges may also differ in various sample types, for example, different body fluids or by different treatments of the sample. One of ordinary skill in the art is capable of considering the relevant factors and establishing appropriate reference ranges for "control values" and "elevated values" of the present invention. For example, a series of samples from control subjects and subjects diagnosed with HCC can be used to establish ranges that are "normal" or "control" levels and ranges that are "elevated" or "higher" than the control range.

Similarly, "reduced levels" or "lower levels" as used herein refer to levels of circulating miRNA that are lower than what would normally be observed in a comparable sample from control or normal subjects (i.e., a reference value). In some embodiments, "control levels" (i.e. normal levels) refer to a range of circulating miRNA levels that would be normally be expected to be observed in a mammal that does not have a neoplastic disease and "reduced levels" refer to circulating miRNAs that are below the range of such control levels.

The level of one or more miRNAs measured in the test sample is normalized, such as by comparison to an internal reference nucleic acid, e.g., small RNA U6. The normalized levels of the one or more miRNAs may then be compared to a reference value to determine if the levels of the one or more miRNAs are elevated or reduced relative to the reference value. Typically, the reference value is the normalized level of the same miRNA measured in a comparable sample from one or more healthy individuals or individuals with chronic liver disease. An increase or decrease in the level of the one or more miRNAs relative to the reference value may be used in conjunction with clinical factors to diagnose HCC.

In some embodiments, the level of one or more circulating miRNAs is combined with one or more additional HCC markers to improve diagnostic sensitivity and specificity. Exemplary HCC markers may be circulating or non-circulating and may include, but are not limited to α-Fetoprotein (AFP) and des-gamma carboxyprothrombin. AFP, a glycoprotein, is a serum biochemical marker for detection of HCC. However, AFP elevations are associated not only with HCC, but with acute and chronic liver disease as well (Lok A S, Lai C L. *Hepatology* 1989, 9:110-115; Yuen M F, Lai C L. *Best Prac Res Clin Gastroenterol* 2005, 19:91-99; Yuen M F, Lai C L. *Ann Oncol* 2003, 14:1463-1467; Di Bisceglie et al. *J Hepatol.* 2005). Thus, AFP has limited utility for detecting HCC, especially in the early stages. Recently, *Lens culinaris* agglutinin-reactive AFP (AFP-L3) and des-gamma-carboxyprothrombin (DCP), also known as prothrombin induced by vitamin k absence-II (PIVKA-II), have been reported to be effective in early detection of HCC. AFP-L3 is the main glycoform of AFP in the serum of HCC patients. Measurement of AFP-L3 as a percentage of total AFP helps distinguish non-malignant hepatic disease from HCC, the assessment of therapeutic effects, and predicting the prognosis of HCC (Oka et al. *J Gastroenterol Hepatology.* 2001; 16:1378-1383; Shiraki et al. *Hepatology* 1995; 22:802-807; Miyaaki et al. *J. Gastroenterol.* 2007; 42:962-968; Yoshida et al. *International J of Oncol.* 2002, 20:305-309).

DCP is an abnormal prothrombin that lack coagulating activity. It has been suggested that DCP concentration may also help to differentiate benign liver diseases and HCC. DCP has even been reported to be more sensitive and specific in diagnosing CC when compared to AFP, especially in Eastern Asian counties and in North America, however, these results have not been shown in Europe (Ikoma et al. *Hepatogastro-enterology.* 2002, 49:235-238; Gomaa et al. *World J Gastroenterol* 2009; 15(11):1301-1314).

Multiple studies have evaluated the performance characteristics of AFP, AFP-L3 and DCP in the diagnosis of HCC. These studies showed sensitivities of 77-88% and specificities of 59-91%, with differences most likely be due to the high dependency on cut-off values for each marker (Ikoma et al. *Hepatogastro-enterology.* 2002, 49:235-238; Sterling et al. Toyoda et al. *Clinic Gastroenterol Hepatol.* 2006, 4:111-117; Volk et al. *Cancer Biomark.* 2007, 3:79-87). These studies also showed that dependable biomarkers for early detection of HCC have remained elusive. Current diagnosis of HCC is based on imaging technology and serum AFP levels. The present methods advantageously improve early diagnosis of HCC. Methods for measuring AFP, AFP-L3, and DCP are known in the art. For example, total AFP, AFP-L3, and DCP serum levels can be measured using two commercially available kits in the LiBASys automated immunological analyzer (Wako Chemicals USA Inc. Richmond, Va.). AFP and AFP-L3 can be measured simultaneously using a liquid-phase binding reaction between antigen and antibody, with separation of bound and free forms by anion exchange column chromatography. An exemplary DCP assay is based on anti-DCP monoclonal antibodies and anti-prothrombin monoclonal antibodies, and a substrate for fluorophotometric measurement.

The circulating miRNA level in a test sample can be used in conjunction with clinical factors other than circulating miRNA to diagnose a disease. Clinical factors of particular relevance in the diagnosis of liver disease include, but are not limited to, the patient's medical history, a physical examination of the patient, and liver enzymes. In some embodiments, the level of one or more circulating miRNAs is combined with one or more additional liver disease markers to improve diagnostic sensitivity and specificity. Exemplary liver disease markers include, but are not limited to ALT, AST, ALP, bilirubin, and serum albumin.

Alanine transaminase (ALT), also called Serum Glutamic Pyruvate Transaminase (SGPT) or Alanine aminotransferase (ALAT) is an enzyme present in hepatocytes (liver cells). When a cell is damaged, it leaks this enzyme into the blood, where it is measured. ALT rises dramatically in acute liver damage, such as viral hepatitis or paracetamol (acetaminophen) overdose. Elevations are often measured in multiples of the upper limit of normal (ULN). Aspartate transaminase (AST), also called Serum Glutamic Oxaloacetic Transaminase (SGOT) or aspartate aminotransferase (ASAT), is similar to ALT in that it is another enzyme associated with liver parenchymal cells. It is raised in acute liver damage, but is also present in red blood cells, and cardiac and skeletal muscle and is therefore not specific to the liver. The ratio of AST to ALT is sometimes useful in differentiating between causes of liver damage. Alkaline phosphatase (ALP) is an enzyme in the cells lining the biliary ducts of the liver. ALP levels in plasma will rise with large bile duct obstruction, intrahepatic cholestasis or infiltrative diseases of the liver. Bilirubin is a breakdown product of heme (a part of hemoglobin in red blood cells). The liver is responsible for clearing the blood of bilirubin. It does this by the following mechanism: bilirubin is taken up into hepatocytes, conjugated (modified to make it water-soluble), and secreted into the bile, which is excreted into the intestine.

Determining Effectiveness of Therapy or Prognosis

In one aspect, the level of one or more circulating miRNAs in a biological sample of a patient is used to monitor the effectiveness of treatment or the prognosis of disease. In some embodiments, the level of one or more circulating miRNAs in a test sample obtained from a treated patient can be compared to the level from a reference sample obtained from that patient prior to initiation of a treatment. Clinical monitoring of treatment typically entails that each patient serve as his or her own baseline control. In some embodiments, test samples are obtained at multiple time points following administration of the treatment. In these embodiments, measurement of level of one or more circulating miRNAs in the test samples provides an indication of the extent and duration of in vivo effect of the treatment.

A prognosis may be expressed as the amount of time a patient can be expected to survive. Alternatively, a prognosis may refer to the likelihood that the disease goes into remission or to the amount of time the disease can be expected to remain in remission. Prognosis can be expressed in various ways; for example, prognosis can be expressed as a percent chance that a patient will survive after one year, five years, ten years or the like. Alternatively, prognosis may be expressed as the number of years, on average that a patient can expect to survive as a result of a condition or disease. The prognosis of a patient may be considered as an expression of relativism, with many factors affecting the ultimate outcome. For example, for patients with certain conditions, prognosis can be appropriately expressed as the likelihood that a condition may be treatable or curable, or the likelihood that a disease will go into remission, whereas for patients with more severe conditions prognosis may be more appropriately expressed as likelihood of survival for a specified period of time. Additionally, a change in a clinical factor from a baseline level may impact a patient's prognosis, and the degree of change in level of the clinical factor may be related to the severity of adverse events. Statistical significance is often determined by comparing two or more populations, and determining a confidence interval and/or a p value.

Multiple determinations of circulating miRNA levels can be made, and a temporal change in activity can be used to determine a prognosis. For example, comparative measurements are made of the circulating miRNA of an acellular body fluid in a patient at multiple time points, and a comparison of a circulating miRNA value at two or more time points may be indicative of a particular prognosis.

In certain embodiments, the levels of activity of one or more circulating miRNAs are used as indicators of an unfavorable prognosis. According to the method, the determination of prognosis can be performed by comparing the measured circulating miRNA level to levels determined in comparable samples from healthy individuals or to levels known to corresponding with favorable or unfavorable outcomes. The circulating miRNA levels obtained may depend on an number of factors, including, but not limited to, the laboratory performing the assays, the assay methods used, the type of body fluid sample used and the type of disease a patient is afflicted with. According to the method, values can be collected from a series of patients with a particular disorder to determine appropriate reference ranges of circulating miRNA for that disorder. One of ordinary skill in the art is capable of performing a retrospective study that compares the determined levels to the observed outcome of the patients and establishing ranges of levels that can be used to designate the prognosis of the patients with a particular disorder. For example, levels in the lowest range would be indicative of a more favorable prognosis, while circulating miRNA levels in the highest ranges would be indicative of an unfavorable prognosis. Thus, in this aspect the term "elevated levels" refers to levels of that are above the range of the reference value. In some embodiments patients with "high" or "elevated" levels have levels that are higher than the median activity in a population of patients with that disease. In certain embodiments, "high" or "elevated" levels for a patient with a particular disease refers to levels that are above the median values for patients with that disorder and are in the upper 40% of patients with the disorder, or to levels that are in the upper 20% of patients with the disorder, or to levels that are in the upper 10% of patients with the disorder, or to levels that are in the upper 5% of patients with the disorder.

Because the level of circulating miRNA in a test sample from a patient relates to the prognosis of a patient in a continuous fashion, the determination of prognosis can be performed using statistical analyses to relate the determined circulating miRNA levels to the prognosis of the patient. A skilled artisan is capable of designing appropriate statistical methods. For example, the methods may employ the chi-squared test, the Kaplan-Meier method, the log-rank test, multivariate logistic regression analysis, Cox's proportional-hazard model and the like in determining the prognosis. Computers and computer software programs may be used in organizing data and performing statistical analyses. The approach by Giles et. al., *British Journal of Hemotology,* 121:578-585, is exemplary. As in Giles et al., associations between categorical variables (e.g., miRNA levels and clinical characteristics) can be assessed via cross-tabulation and Fisher's exact test. Unadjusted survival probabilities can be estimated using the method of Kaplan and Meier. The Cox proportional hazards regression model also can be used to assess the ability of patient characteristics (such as miRNA levels) to predict survival, with 'goodness of fit' assessed by the Grambsch-Therneau test, Schoenfeld residual plots, martingale residual plots and likelihood ratio statistics (see Grambsch et al, 1995). In some embodiments, this approach can be adapted as a simple computer program that can be used with personal computers or personal digital assistants (PDA). The prediction of patients' survival time in based on their circulating miRNA levels can be performed via the use of a visual basic for applications (VBA) computer program developed within Microsoft® Excel. The core construction and analysis may be based on the Cox proportional hazard models. The VBA application can be developed by obtaining a base hazard rate and parameter estimates. These statistical analyses can be performed using a statistical program such as the SAS® proportional hazards regression, PHREG, procedure. Estimates can then be used to obtain probabilities of surviving from one to 24 months given the patient's covariates. The program can make use of estimated probabilities to create a graphical representation of a given patient's predicted survival curve. In certain embodiments, the program also provides 6-month, 1-year and 18-month survival probabilities. A graphical interface can be used to input patient characteristics in a user-friendly manner.

In some embodiments of the invention, multiple prognostic factors, including circulating miRNA level, are considered when determining the prognosis of a patient. For example, the prognosis of a cancer patient may be determined based on circulating miRNA and one or more prognostic factors selected from the group consisting of cytogenetics, performance status, age, gender and previous diagnosis. In certain embodiments, other prognostic factors may be combined with the circulating miRNA level or other biomarkers in the algorithm to determine prognosis with greater accuracy.

Kits

A kit may be used for conducting the diagnostic and prognostic methods described herein. Typically, the kit should contain, in a carrier or compartmentalized container, reagents useful in any of the above-described embodiments of the diagnostic method. The carrier can be a container or support, in the form of, e.g., bag, box, tube, rack, and is optionally compartmentalized. The carrier may define an enclosed confinement for safety purposes during shipment and storage. In one embodiment, the kit includes one or more PCR primers capable of amplifying miR-16, miR-199a, and/or miR-195. The primers may be labeled with a detectable marker such as radioactive isotopes, or fluorescence markers. Instructions for using the kit or reagents contained therein are also included in the kit.

EXAMPLE

The present methods and kits, thus generally described, will be understood more readily by reference to the following examples, which are provided by way of illustration and are not intended to be limiting of the present methods and kits. The following is a description of the materials and experimental procedures used in the example.

Materials and Methods

Study Subjects. A total of 283 subjects were studied. The first group consisted of 105 patients with liver cirrhosis complicated by HCC. The diagnosis of HCC was confirmed by biopsy and histological evaluation or detection of new hepatic lesion with arterial phase enhancement on computed tomography or magnetic resonance imaging. The second group included 107 patients with chronic liver diseases (CLDs) and no HCC. All patients had biopsies reviewed by a pathologist, fibrosis staging between 0 and 4 (metavir scale), and variable degrees of inflammation. The clinical follow up in this group included ultrasound and AFP measurement every 6 months for at least 2 years with no evidence of development of HCC. All HCC and CLD patient samples were obtained from the Liver Center, Harvard Medical School, Boston, Mass. A third group of 71 apparently healthy adults with no known hepatitis or liver diseases was recruited at Quest Diagnostics Nichols Institute, San Juan Capistrano, Calif. All samples were collected with IRB-approved protocol and consent forms. The samples were peripheral blood collected in red top-tubes; serum was isolated by centrifugation and stored at −80° C. until analysis.

Isolation of miRNA. Total RNA, including low molecular weight RNA, was isolated from 0.5 mL of patient serum on the NucliSens easyMAG system (Biomeriux SA, France) according to the manufacturer's protocol.

Semi-quantitative Reverse-Transcriptase PCR Analysis of miRNA. Two-step TaqMan reverse-transcriptase PCR analysis was performed for analysis of miRNAs. Reverse transcription was performed in a 15-μl reaction volume using specific primers for each miRNA contained in the TaqMan MiRNA Reverse Transcription kit (Applied Biosystems, Foster City, Calif.) by sequentially incubating at 16° C. for 30 min, 42° C. for 30 min, and 85° C. for 5 min. Real-time PCR was done using the standard TaqMan MiRNA assay protocol on an Applied Biosytems 7900 Fast real time PCR system (Applied Biosystems). Each PCR mixture (20 μl) included the reverse transcription products, TaqMan 2× Universal PCR Master Mix without UNG Amperase, miRNA-specific TaqMan probes, and primers supplied by Applied Biosystems. The reactions were incubated in a 96-well plate with an initial denaturation at 95° C. for 10 min, followed by 40 cycles of 95° C. for 15 s and 60° C. for 1 min. The level of miRNA expression was measured using the threshold cycle (Ct), the fractional cycle number at which the fluorescence of each sample passes a fixed threshold (i.e. when the amount of synthesized DNA becomes exponential). Thus, higher Ct values reflect lower miRNA expression; a Ct value of 40 (i.e., the number of PCR cycles performed) indicates no expression. miRNA expression levels were normalized using an endogenous small RNA control U6 (Applied Biosystems). The expression of miRNA relative to small RNA U6 is reported as ΔCt, which is calculated by subtracting the Ct of U6 RNA from the Ct of target miRNA.

Measurement of Total AFP, AFP-L3, and DCP. Total AFP, AFP-L3, and DCP serum levels were measured using two commercially available kits in the LiBASys automated immunological analyzer (Wako Chemicals USA Inc. Richmond, Va.). AFP and AFP-L3 were measured simultaneously using a liquid-phase binding reaction between antigen and antibody, with separation of bound and free forms by anion exchange column chromatography. The cutoff value of AFP for HCC was set at 20 ng/mL, the most commonly used clinical cutoff value. The cutoff value of AFP-L3% for HCC was set at 10%, as indicated by the kit manufacturer and verified by our laboratory. The DCP assay is based on anti-DCP monoclonal antibodies and anti-prothrombin monoclonal antibodies, and a substrate for fluorophotometric measurement. The DCP cutoff for HCC was 7.5 ng/ml, as indicated by the kit manufacturer and verified by our laboratory (data not shown).

Statistical Analyses. Student's t test was used to compare the serum level of each marker between HCC, CLD, and normal control groups. Associations between each marker and HCC were assessed using logistic regression analysis. miRNA cutoff values for distinguishing HCC from non-HCC CLD were determined according to miRNA distribution curves in each group. The sensitivity and specificity of each marker combination for distinguishing HCC from non-HCC CLD were compared with McNemar's test. P values<0.05 were considered statistically significant.

Results

Study Subjects. The demographic and clinical characteristics of the HCC and CLD groups are summarized in Table 1. All patients with HCC had underlying cirrhosis as determined by biopsy. HCV infection was the most common underlying condition among HCC and non-HCC CLD patients.

TABLE 1

Clinical Characteristic of Study Subjects

|  | Hepatocellular Carcinoma | Chronic Liver Diseases |
|---|---|---|
| Number | 105 | 107 |
| Age, Median (Range) | 55 (25-80) yr | 51 (19-75) yr |
| Male, n (%) | 88 (83.8) | 68 (63.9) |
| Etiology, n (%) | | |
| HBV | 20 (19.1) | 8 (7.5) |
| HCV | 66 (62.9) | 59 (55.1) |
| HBV, HCV | 1 (0.9) | 0 |
| Other[a] | 18 (17.1) | 40 (37.4) |
| Metavir, n (%) | | |
| 0 | NA[b] | 11 (10.3) |
| 1 | NA | 27 (25.2) |
| 2 | NA | 8 (7.5) |
| 3 | NA | 14 (13.1) |
| 4 | NA | 47 (43.9) |
| Tumor Size, n (%) | | |
| ≤3 cm | 43 (40.9) | NA[b] |
| >3 cm | 62 (59.1) | NA |

[a]Others includes alcohol and nonalcoholic steatohepatitis
[b]NA, not applicable miRNA Screening. The serum levels of 7 miRNAs: miR-1, miR-16, miR-122a, miR-139, miR-195, miR-199a, miR-224 were assessed to determine whether these markers were present in serum at levels adequate for laboratory utility. Levels of each miRNA were measured in pooled sera from at least 10 normal healthy individuals and HCC (Table 2). miR-1, miR-122a, miR-139, and miR224 exhibited extremely low or undetectable expression (i.e., high Ct values) in both normal and patient sera. Therefore, only MiR-16, miR-195, and miR-199a were chosen for further investigation.

TABLE 2 miRNA Screening in Patients with HCC and Normal Individuals

| | Ct Values[a] | | | | | | | |
|---|---|---|---|---|---|---|---|---|
| Group | U6 | MiR1 | MiR-16 | MiR-195 | MiR-199a | MiR224 | MiR139 | MiR122a |
| Normal | | | | | | | | |
| Normal 1 | 26.2 | 40.0 | 27.0 | 37.0 | 32.4 | 40.0 | 40.0 | 40.0 |
| Normal 2 | 26.8 | 39.3 | 27.0 | 36.3 | 32.8 | 38.6 | 40.0 | 40.0 |
| Normal 3 | 29.7 | 40.0 | 26.8 | 36.8 | 32.6 | 38.1 | 40.0 | 40.0 |

TABLE 2-continued miRNA Screening in Patients with HCC and Normal Individuals

| Group | Ct Values[a] | | | | | | | |
|---|---|---|---|---|---|---|---|---|
| | U6 | MiR1 | MiR-16 | MiR-195 | MiR-199a | MiR224 | MiR139 | MiR122a |
| Normal 4 | 26.0 | 36.2 | 28.3 | 37.7 | 34.2 | 38.9 | 40.0 | 40.0 |
| Normal pool | 26.0 | 37.1 | 26.8 | 35.8 | 33.4 | 38.9 | 39.7 | 40.0 |
| Mean | 26.9 | 38.5 | 27.2 | 36.7 | 33.1 | 38.9 | 39.9 | 40.0 |
| SD | 1.6 | 1.8 | 0.6 | 0.7 | 0.7 | 0.7 | 0.1 | 0.0 |
| HCC[b] | | | | | | | | |
| HCC pool 1 | 26.6 | 39.7 | 28.7 | 39.8 | 34.9 | 40.0 | 40.0 | 40.0 |
| HCC pool 2 | 25.0 | 40.0 | 28.6 | 38.5 | 36.3 | 38.2 | 40.0 | 40.0 |
| HCC pool 3 | 24.6 | 40.0 | 29.0 | 37.5 | 35.8 | 40.0 | 40.0 | 40.0 |
| Mean | 25.4 | 39.9 | 28.8 | 38.6 | 35.7 | 39.4 | 40.0 | 40.0 |
| SD | 1.1 | 0.2 | 0.2 | 1.2 | 0.7 | 1.0 | 0.0 | 0.0 |

[a]The Ct is the fractional cycle number at which the fluorescence of each sample passes a fixed threshold. Higher Ct values indicate lower expression levels; a Ct value of 40 indicates no expression.
[b]All sera used for HCC pools had elevated AFP and AFP-L3% levels.

Serum Levels of miRNAs and Conventional HCC Markers. Serum levels of miR-16, miR-199a, and miR-195, were significantly lower in HCC patients than in the CLD and control groups (i.e., indicated by higher Ct values) and this results in a higher ΔCt following normalization to the U6 internal control, (Table 3). CLD patients also had significantly lower levels of all 3 miRNAs than did normal control subjects (Tables 2) and this also results in higher ΔCt following normalization to the U6 internal control, (Table 3). Serum levels of AFP, AFP-L3, and DCP were significantly higher in HCC patients than in both the CLD and normal control group; only AFP was significantly higher in CLD than in control subjects (Table 3). Consistent with the results presented above, univariate logistic regression analysis demonstrated that levels of miR-16, miR-199a, AFP, AFP-L3%, DCP, and miR 95 were significantly associated with HCC (Table 4).

TABLE 4

Univariate Logistic Regression Analysis for Differentiating HCC from CLD

| Variable | AUC | Coefficient | Chi-Square | Coefficient P | Coefficient (95% CI) |
|---|---|---|---|---|---|
| miR-16 | 0.8683 | 0.35 | 36.49 | <0.01 | 0.24-0.47 |
| miR-195 | 0.6863 | 0.11 | 4.29 | 0.04 | 0.01-0.22 |
| miR-199a | 0.7934 | 0.39 | 25.9 | <0.01 | 0.25-0.56 |
| AFP | 0.8908 | 0.06 | 17.1 | <0.01 | 0.04-0.09 |
| AFP-L3 | 0.7193 | 0.05 | 14.3 | <0.01 | 0.03-0.09 |
| DCP | 0.8212 | 0.27 | 13.3 | <0.01 | 0.15-0.44 | miRNA Cutoff Values for Differentiating HCC from non-HCC CLD. Cutoff values (ΔCt) for each miRNA were determined according to distribution curves of the HCC and CLD groups (FIG. 1), with the cutoff being the intersection

TABLE 3

Median Levels of miRNAs and Conventional Biomarkers in HCC, CLD, and Control Groups

| Marker | HCC (n = 105) | CLD (n = 107) | Normal (n = 71) | HCC vs. CLD | HCC vs. Normal | CLD vs. Normal |
|---|---|---|---|---|---|---|
| | Median (range) | | | P value[b] | | |
| MiRNA, ΔCt[a] | | | | | | |
| miR-16 | 7.4 (−1.4-16.7) | 4.1 (−4.3-16.4) | 0.9 (−4.8-9.8) | <0.01 | <0.01 | <0.01 |
| miR-195 | 13.3 (4.6-17.3) | 12.8 (4.3-18.8) | 9.5 (4.2-15.1) | 0.04 | <0.01 | <0.01 |
| miR-199a | 10.7 (2.9-15.5) | 9.1 (1.9-13.4) | 6.9 (0.2-11.1) | <0.01 | <0.01 | <0.01 |
| Biomarker | Mean (range; median) | | | P value[b] | | |
| AFP, ng/mL | 10,527.5 (0.8-293,100.0; 28.5) | 5.1 (0.1-74.3; 1.6) | 2.5 (0.1-8.8; 2.6) | <0.01 | <0.01 | 0.03 |
| AFP-L3, % | 21.5 (0.1-96.7; 0.1) | 1.75 (0.1-99.5; 0.1) | 0.1 (0.1-0.1; 0.1) | <0.01 | <0.01 | 0.13 |
| DCP, ng/mL | 165.9 (0.1-4,790.0; 5.4) | 0.7 (0.1-24.2; 0.1) | 0.5 (0.1-3.8; 0.1) | <0.01 | <0.01 | 0.40 |

[a]ΔCt, difference in cycle threshold (Ct) between target and internal control (small RNA U6). Higher ΔCt values indicate lower miRNA expression levels in the subject samples.
[b]P values were calculated by Student's t test.

of the two curves. miR-16 allowed the best separation between groups (ΔCt cutoff=6), followed by miR-199a (ΔCt cutoff=10). miR-195 provided virtually no separation between HCC and CLD groups and was thus excluded from further analyses.

Accuracy of miRNAs, AFP, AFP-L3%, and DCP for Differentiating HCC from CLD. Table 5 presents the accuracy of the miRNAs for differentiating HCC from CLD, alone and in combination with conventional serum markers of HCC. miRNA and conventional marker values above their respective cutoff values indicate a high probability of HCC. As a single marker, miR-16 had the highest sensitivity for detecting HCC, followed by miR-199a, AFP, DCP, and AFP-L3% (Table 5). This pattern was also observed when analysis was limited to HCC cases with small tumors (≤3 cm) (Table 5).

TABLE 5

Comparison of miRNAs and HCC Markers for Differentiating Hepatocellular Carcinoma from Chronic Liver Diseases

| | Sensitivity, % | | | |
|---|---|---|---|---|
| | HCC Total (n = 105) | HCC tumor <3 cm (n = 43) | HCC tumor >3 cm (n = 62) | Specificity (%) |
| AFP | 59.0 | 37.2 | 72.6 | 93.4 |
| AFP-L3% | 36.2 | 4.7 | 56.5 | 97.2 |
| DCP | 46.7 | 20.9 | 62.9 | 98.1 |
| miR-16 | 72.1 | 79.1 | 66.1 | 88.8 |
| miR-199a | 62.9 | 72.1 | 56.5 | 74.8 |
| miR-199a, miR-16$^a$ | 78.1 | 88.4 | 71.0 | 64.5 |
| AFP, AFP-L3%, DCP$^a$ | 75.2 | 75.2 | 90.3 | 89.7 |
| AFP, AFP-L3%, DCP, miR-16$^a$ | 92.4 | 92.4 | 93.5 | 78.5 |
| AFP, AFP-L3%, DCP, miR-199a$^a$ | 92.4 | 88.4 | 95.2 | 65.4 |
| AFP, AFP-L3%, DCP, miR-16, miR-199a$^a$ | 94.3 | 93.0 | 95.2 | 55.1 |
| miR-16, AFP$^a$ | 87.6 | 86.0 | 87.1 | 82.2 |
| miR-16, AFP, AFP-L3%$^a$ | 89.5 | 86.0 | 90.3 | 80.4 |
| miR-16, AFP, DCP$^a$ | 91.4 | 88.4 | 91.9 | 80.4 |

$^a$At least one of the listed analytes was above the cutoff value.

For analysis of marker combinations, a positive result on at least 1 marker was considered to indicate HCC. The combination of miR-16 with AFP, AFP-L3, and DCP identified 97 of 105 (92.4%) HCC cases, with 78.5% specificity. This combination resulted in significantly improved sensitivity when compared with the 3 HCC markers alone (AFP, AFP-L3, and DCP, p<0.01). The addition of miR-199a to the combination allowed detection of only 2 additional HCC cases (94.3% sensitivity), at the expense of a marked decrease in specificity (55.1%). When analysis of HCC patients was restricted to those with small tumors (≤3 cm), miR-16 identified 34 (79.1%) of 43 patients, with 88.8% specificity. The combination of miR-16, AFP, AFP-L3%, and DCP still yielded significantly greater sensitivity than the 3 HCC marker combination (92.4 vs. 75.2%, p<0.01). For HCC patients with large tumors (>3 cm), of the addition of miR-16 did not significantly improve sensitivity or specificity of HCC detection relative to the 3-marker combination of AFP, AFP-L3%, and DCP (all P>0.05, Table 5).

miRNA Measurement as a Second-Line Test for HCC Screening. The 3-marker combination of AFP, AFP-L3, and DCP provides high specificity but relatively low sensitivity for HCC, especially in patients with small tumors. The utility of miRNA measurement as a second-line test for HCC screening among patients with normal levels of AFP, AFP-L3%, and DCP (26 HCC and 96 CLD patients; Table 6) was analyzed. Again, miR-16 ΔCt values above 6 were considered to indicate HCC. Decreased levels of miR-16 identified 18 of the 26 (69.2%) HCC patients overall, including 16 of 21 (76.2%) with small tumors (≤3 cm) and 2 of 5 (40%) with larger tumors. miR-16 was falsely decreased in only 12 of the 96 (12.5%) non-HCC CLD patients. miR-199a measurement provided identical sensitivities, but with a markedly higher false-positive rate (Table 6).

TABLE 6

Positive HCC prediction from AFP,
AFP-L3 and DCP negative cases

| | HCC Total (n = 26) | HCC tumor <3 cm (n = 21) | HCC tumor >3 cm (n = 5) | CLD (n = 96) |
|---|---|---|---|---|
| miR-16 | 69.2% (18) | 76.2% (16) | 40.0% (2) | 12.5% (12) |
| miR-199a | 69.2% (18) | 76.2% (16) | 40.0% (2) | 27.1% (26) |

Data are percent (number) of samples with miRNA ΔCt values above the cutoff among samples with normal results for AFP, AFP-L3%, and DCP.

In conclusion, this study has demonstrated that measurement of serum levels of miR-16 and miR-199a improves differentiation of HCC from non-HCC CLD. The combination of an miRNA such as miR-16 together with measurement of AFP, AFP-L3, and DCP yielded greater sensitivity and specificity for HCC detection than any other single marker or marker combination examined.

REFERENCES

1. Ei-Scrag H B, Rudolph K L. Hepatocellular carcinoma: epidemiology and molecular carcinogenesis. *Gastroenterology.* 2007; 132:2557-2576.
2. Parkin D M, Bray F, Ferlay J, Pisani P. Estimating the world cancer burden: Globocan 2000. *Int J. Cancer.* 2001; 94:153-156.
3. Benson A B 3rd, Abrams T A, Ben-Josef E, et al. NCCN clinical practice guidelines in oncology: hepatobiliary cancers. *J Natl Compr Canc Netw.* 2009; 7350-391.
4. Lee Y S, Dutta A. MiRNAs in cancer. *Annu Rev Pathol.* 2009:4:199-227.
5. Volinia S, Calin G A, Liu C G, et al. A miRNA expression signature of human solid tumors defines cancer gene target. *Proc Natl Acad Sci USA* 2006; 103:2257-2261.
6. Esquela-Kerscher A, Slack F J. OncomiRs-miRNA with a role in cancer. *Nat Rev Cancer.* 2006:6:259-269.
7. Gramantier L, Fornari F, Callegari E, et al. MiRNA involvement in hepatocellular carcinoma. *J Cell Mol Med.* 2008; 12:2189-2204.
8. Kloosterman W, Plasterk R. The diverse functions of miRNAs in animal development and disease. *Dev Cell.* 2006; 11:441-450.
9. Stefani G, Slack F. Small noncoding RNAs in animal development. *Nat Rev Mol Cell Biol.* 2008; 9:219-230.
10. Zamore P, Haley B. Ribo-gnome: the big world of small RNAs. *Science.* 2005; 309:1519-1524.
11. Calin G, Dumitru C, Shimizu M, et al. Frequent deletions and down-regulation of micro-RNA genes miR15 and miR-16 at 13q14 in chronic lymphocytic leukemia. *Proc Natl Acad Sci USA.* 2002; 99:15524-15529.
12. Lu J, Getz G, Miska E A, et al. MiRNA expression profiles classify human cancers. *Nature.* 2005; 435:834-838.

13. Murakami Y, Yasuda T, Saigo K, et al. Comprehensive analysis of miRNA expression pattern in hepatocellular carcinoma and non-tumorous tissues. *Oncogene.* 2006; 25:2537-2545.
14. Huang Y S, Gai Y, Yu X F, et al. Microarray analysis of miRNA expression in hepatocellular carcinoma and non-tumorous tissue without vial hepatitis. *J Gastroenterol Hepatol.* 2008; 23:87-94.
15. Meng F, Henson R, Wehbe-Janck H, et al. MiRNA-21 regulates expression of the PTEN tumor suppressor gene in human hepatocellular cancer. *Gastroenterology.* 2007; 133:647-658.
16. Jiang J, Gusev Y, Aderca I. et al. Association of miRNA expression in hepatocellular carcinomas with hepatitis infection, cirrhosis, and patient survival. *Clin Cancer Res.* 2008; 14:419-427.
17. Fornari F. Gramantieri L, Ferracin M, et al. MiR-221 control CDKN1C/p57 and CDKN1b/p27 expression in human hepatocellular carcinoma. *Oncogene.* 2008:27: 5651-5661.
18. Medina R, Zaidi S K, Liu C G, et al. MiRNAs 221 and 222 bypass quiescence and compromise cell survival. *Cancer Res.* 2008; 68:2773-2780
19. Pei Y, Zhang T, Renault V, et al. An overview of hepatocellular carcinoma study by omics-based methods. *Acta Biochimica et Biophysica Sinica.* 2009; 41:1-15.
20. Kim S, Lee U J, Kim M N, et al. MiRNA miR-199a* regulates the MET proto-oncogene and the downstream extracellular signal-regulated kinase 2 (ERK2).http://www.jbc.org/content/283/26/18158.abstract?ck=nck-fn-2#fn-2 *J Biol Chem.* 2008; 283:18158-18166.
21. Gramantieri L. Ferracin M, Fornari F, et al. Cyclin G1 is a target of miR-122a, a miRNA frequently down-regulated in human hepatocellular carcinoma. *Cancer Res.* 2007; 67:6092-6099.
21b. Bisceglie A D, Sterling R. Chung R, et al. Serum alpha-fetoprotein levels in patients with advanced hepatitis C: results from the HALT-C trial. *J. Hepatol.* 2005; 43:434-441.
22. Li J, Smyth P, Flavin R, et al. Comparison of miRNA expression patterns using total RNA extracted from matched samples of formalin-fixed paraffin-embedded (FFPE) cells and snap frozen cells. *BMC Biotechnol.* 2007; 7:36.
23. Cortez M, Calin G. MiRNA identification in plasma and serum: a new tool to diagnose and monitor diseases. *Expert Opin Biol Ther.* 2009; 9:703-711.
24. Mitchell P S, Parkin R K. Kroh E M, et al. Circulating miRNAs as stable blood-based markers for cancer detection. *Proc Natl Acad Sci USA.* 2008; 105: 10513-10518.
25. Lawrie C, Gal S. Dunlop H, et al. Detection of elevated levels of tumour-associated miRNAs in serum of patients with diffuse large B-cell lymphoma. *Br J Haematol.* 2008; 14: 672-675.
26. Zhu W, Qin W, Atasoy U, et al. Circulating miRNA in breast cancer and healthy subjects. *BMC Res Notes.* 2009; 2:89.
27. Huang Z, Huang D, Ni S, et al. Plasma miRNAs are promising novel biomarkers for early detection of colorectal cancer. *Int J. Cancer.* 2009. [Epub ahead of print]
28. Guo C J, Pan Q, Li D G, et al. miR-15b and miR-16 are implicated in activation of the rat hepatic stellate cell: an essential role for apoptosis. *J Hepatol.* 2009; 50:766-778.
29 Xu T, Zhu Y, Xiong Y, et al. MiRNA-195 suppresses tumorigenicity and regulates G1/S transition of human hepatocellular carcinoma cells. *Hepatology.* 2009; 50:113-121.
30. Datta J, Kutay H, Nasser M, et al. Methylation mediated silencing of miRNA-1 gene and its role in hepatocellular carcinogenesis. *Cancer Res.* 2008; 68:5049-5058.
31. Bruix J, Sherman M; Practice Guidelines Committee, American Association for the Study of Liver Diseases. Management of hepatocellular carcinoma. *Hepatology* 2005:42:1208-1236.
32. Toyoda H, Kumada T, Kiriyama S, et al. Prognostic significance of simultaneous measurement of three tumor markers in patients with hepatocellular carcinoma. *Clin Gastroenterol Hepatol.* 2006; 4:111-117.
33. Volk M L, Hernandez J C, Su G L, et al. Risk factors for hepatocellular carcinoma may impair the performance of biomarkers: a comparison of AFP, DCP, and AFP-L3. *Cancer Biomark* 2007; 3:79-87
34. Filipowicz W, Bhattacharyya S N, Sonenberg N. Mechanisms of post-transcriptional regulation by miRNAs: are the answers in sight? *Nat Rev Genet.* 2008; 9:102-114.
35. Kumar M S, Erkeland S J, Pester R E, et a; Suppression of non-small cell lung tumor development by the let-7 miRNA family. *Cell,* 2007; 131:1109-1169.
36. Calin G, Croce C. MiRNA signature in human cancer. *Nat Rev Cancer.* 2006; 6:857-866.
37. Braconi C, Patel T. MiRNA expression profiling: a molecular tool for defining the phenotype of hepatocellular tumors. *Hepatology.* 2008; 47:1807-1809.
38. Ladeiro Y, Couchy G, Balabaud C, et al. MiRNA profiling in hepatocellular tumors is associated with clinical features and oncogene/tumor suppressor gene mutations. *Hepatology.* 2008; 47:1955-1963.
39. Bonci D, Coppola V, Musumeci M, et al. The miR-15a and miR-16-1 cluster controls prostate cancer progression by targeting multiple oncogenic activities. *Nat Med.* 2008; 14:1271-1277.
40. Bottoni A, Piccin D, Tagliati F, et al. miR-15a and miR-16-1 down-regulation in pituitary adenomas. *J Cell Physiol.* 2005; 204:280-285.
41. Aqeilan R I, Calin G A, Croce C M. miR-15a and miR-16-1 in cancer: discovery, function and future perspectives. *Cell Death Differ.* 2010; 17:215-220.
42. Guo C J, Pan Q, Jiang B, Chen G Y, Li D G. Effects of upregulated expression of miRNA-16 on biological properties of culture-activated hepatic stellate cells. *Apoptosis.* 2009 Sep. 26. [Epub ahead of print]

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A detection method comprising:
  (a) detecting a level of miR-16 miRNA in a serum sample from a human subject diagnosed as having liver cirrhosis by
    (i) performing real-time reverse transcription polymerase chain reaction (RT-PCR) on the serum sample to measure a Ct value for miR-16 miRNA and a control Ct value for U6 small RNA, wherein the Ct value is measured using a detectably labeled probe specific for each miRNA assayed; and
    (ii) calculating a delta Ct value by subtracting the U6 control Ct value from the miR-16 Ct value; and
  (b) detecting at least one of the level of α-fetoprotein (AFP), the level of des-gamma-carboxyprothrombin (DCP), and the percentage of AFP-L3 in the serum sample by
    (i) contacting the serum sample with an antibody that binds to AFP, an antibody that binds to DCP and/or an antibody that binds to AFP-L3; and
    (ii) detecting the binding between AFP and the antibody that binds to AFP, the binding between DCP and the antibody that binds to DCP and/or the binding between AFP-L3 and the antibody that binds to AFP-L3.

2. The method of claim 1, wherein the level of miR-16, AFP, and DCP, and the percentage of AFP-L3 are detected in the sample.

3. The method of claim 1, wherein the level of AFP, the percentage AFP-L3, and the level of des-gamma-carboxyprothrombin (DCP) in the serum sample is greater than a reference value.

4. The method of claim 3, wherein the reference value for: AFP is 20 ng/mL, percentage AFP-L3 is 10%, and DCP is 7.5 ng/ml.

5. The method of claim 1, wherein the delta Ct value is greater than 6.

* * * * *